(12) United States Patent
Bornzin

(10) Patent No.: US 7,286,874 B1
(45) Date of Patent: Oct. 23, 2007

(54) ENSEMBLE AVERAGING FOR EVOKED RESPONSES

(75) Inventor: Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 386 days.

(21) Appl. No.: 10/667,112

(22) Filed: Sep. 17, 2003

(51) Int. Cl.
*A61N 1/362* (2006.01)
*A61B 5/0402* (2006.01)

(52) U.S. Cl. ............... 607/17; 607/9; 607/18; 607/27; 607/28; 600/509; 600/554

(58) Field of Classification Search ............ 607/9, 607/17, 27, 28; 600/509, 554
See application file for complete search history.

(56) References Cited

U.S. PATENT DOCUMENTS

| | | | |
|---|---|---|---|
| 4,340,065 A | 7/1982 | Gessman | |
| 4,551,018 A | 11/1985 | Mannava et al. | |
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,974,598 A | 12/1990 | John | |
| 5,178,154 A | 1/1993 | Ackmann et al. | |
| 5,235,976 A | 8/1993 | Spinelli | 607/25 |
| 5,300,093 A | 4/1994 | Koestner et al. | |
| 5,350,410 A * | 9/1994 | Kleks et al. | 607/28 |
| 5,415,171 A | 5/1995 | Goh et al. | |
| 5,458,623 A | 10/1995 | Lu et al. | 607/28 |
| 5,466,254 A | 11/1995 | Helland | 607/123 |
| 5,476,483 A | 12/1995 | Bornzin et al. | 607/17 |
| 5,540,727 A | 7/1996 | Tockman et al. | 607/18 |
| 5,792,195 A | 8/1998 | Carlson et al. | 607/17 |
| 5,954,661 A | 9/1999 | Greenspon et al. | |
| 6,058,329 A | 5/2000 | Salo et al. | 607/17 |
| 6,314,323 B1 | 11/2001 | Ekwall | 607/23 |
| 6,663,572 B2 | 12/2003 | Starobin et al. | |
| 6,671,548 B1 | 12/2003 | Mouchawar et al. | |
| 6,731,985 B2 * | 5/2004 | Bradley et al. | 607/28 |
| 2001/0037069 A1 | 11/2001 | Carlson et al. | |
| 2002/0032469 A1 | 3/2002 | Marcovecchio | |

FOREIGN PATENT DOCUMENTS

WO    WO9936769    7/1999

* cited by examiner

*Primary Examiner*—Carl Layno
*Assistant Examiner*—Shevon E Johnson

(57) ABSTRACT

Exemplary methods and devices for analyzing intracardiac electrocardiograms (IEGMs) using ensemble averaging and/or an ensemble average. Various methods and/or devices are suitable for use with atrial and/or ventricular autocapture. Other methods, devices and/or systems are also disclosed.

18 Claims, 21 Drawing Sheets

EXEMPLARY METHOD

ENSEMBLE AVERAGING FOR EVOKED RESPONSES

CROSS-REFERENCE TO RELATED APPLICATIONS

This application is related to copending U.S. patent application Ser. No. 10/665,317, titled "Statistical Analysis for Implantable Cardiac Devices" filed Sep. 17, 2003.

TECHNICAL FIELD

Exemplary methods and/or devices presented herein generally relate to cardiac pacing and/or stimulation therapy. Various exemplary methods and/or devices concern ensemble averaging and/or other techniques for analyzing evoked responses.

BACKGROUND

Many implantable pacing devices rely on pacing schemes that sense atrial and/or ventricular activity. For example, a dual chamber pacing device may deliver an atrial stimulus, sense for an atrial response, and then deliver a ventricular stimulus and sense for a ventricular response. In pacing, an "evoked response" results when a delivered stimulus sufficiently "captures" or electrically activates cardiac tissue. Capture typically involves depolarization followed by contraction of one or more chambers. Of course, the ability of cardiac tissue to respond to a stimulus depends on the tissue's activity state. For instance, cardiac tissue in a refractory state typically will not respond to a stimulus. In addition, stimulus power (e.g., magnitude, duration, polarity, etc.) may determine whether a stimulus results in capture. For example, a stimulus delivered at a first power level may not depolarization sufficient tissue to lead to capture; whereas, a slightly higher power level may depolarize sufficient tissue to lead to capture. The power level at which capture occurs (e.g., in nonrefractory tissue), is typically referred to as the capture, pacing, or stimulation threshold. Various pacing schemes, generally referred to as "autocapture" schemes, aim to discern atrial and/or ventricular stimulation thresholds. Pacing at and/or near the stimulation threshold can conserve energy and, hence, increase device and/or power supply longevity.

Thus, for a variety of reasons, an implantable pacing device benefits from an ability to discern capture from noncapture. In addition, an implantable pacing device can benefit from an ability to discern native cardiac activity and/or fusion and/or pseudofusion during pacing. Fusion and/or pseudofusion may occur when native activity exists during pacing. Fusion is typically characterized by depolarization of the myocardium initiated by both a non-native stimulus and a native stimulus. Pseudofusion is typically characterized by depolarization of the myocardium initiated by a native stimulus; however, a non-native stimulus, that does not significantly contribute to depolarization, is present that distorts a sensed depolatization/repolarization wave complex. Because fusion and pseudofusion can distort sensed activity, the presence of fusion and/or pseudofusion can interfere with diagnosis of capture and/or noncapture.

Another issue typically encountered in detection of capture and/or noncapture (and/or fusion, pseudofusion, etc.) involves post-stimulus polarization of one or more sensing electrodes, which is sometimes referred to herein as "afterpotential". Post-stimulus electrode polarization stems primarily from capacitive charging of an electrode-electrolyte interface during delivery of a pacing stimulus. Upon termination of the pacing stimulus, the post-stimulus electrode polarization decays over time, generally in an exponential fashion like a capacitor. Characteristics of post-stimulus electrode polarization generally depend on a variety of parameters, such as, electrode materials, electrode geometry, tissue characteristics, tissue contact, stimulation energy, and others, many of which vary over time. Because post-stimulus polarization may severely interfere with response sensing, detection and/or characterization, many implantable pacing devices use low polarization electrodes and/or leads, blanking periods, and/or special circuitry to minimize artifacts arising from post-stimulus electrode polarization.

Various exemplary methods and/or devices described herein enhance detection and/or characterization of cardiac activity. In particular, such methods and/or devices address signal-to-noise, electrode polarization and/or other issues related to detection and/or characterization of cardiac activity.

SUMMARY

Exemplary methods and devices for analyzing intracardiac electrocardiograms (IEGMs) using ensemble averaging and/or an ensemble average. Various methods and/or devices are suitable for use with atrial and/or ventricular autocapture. Other methods, devices and/or systems are also disclosed.

Various exemplary devices for performing such exemplary methods are also disclosed herein along with a variety of other exemplary methods and/or devices. In general, the various devices and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

The techniques described below are intended to be implemented in connection with any stimulation device that is configured or configurable to stimulate nerves and/or stimulate and/or shock a patient's heart.

Figure 1:
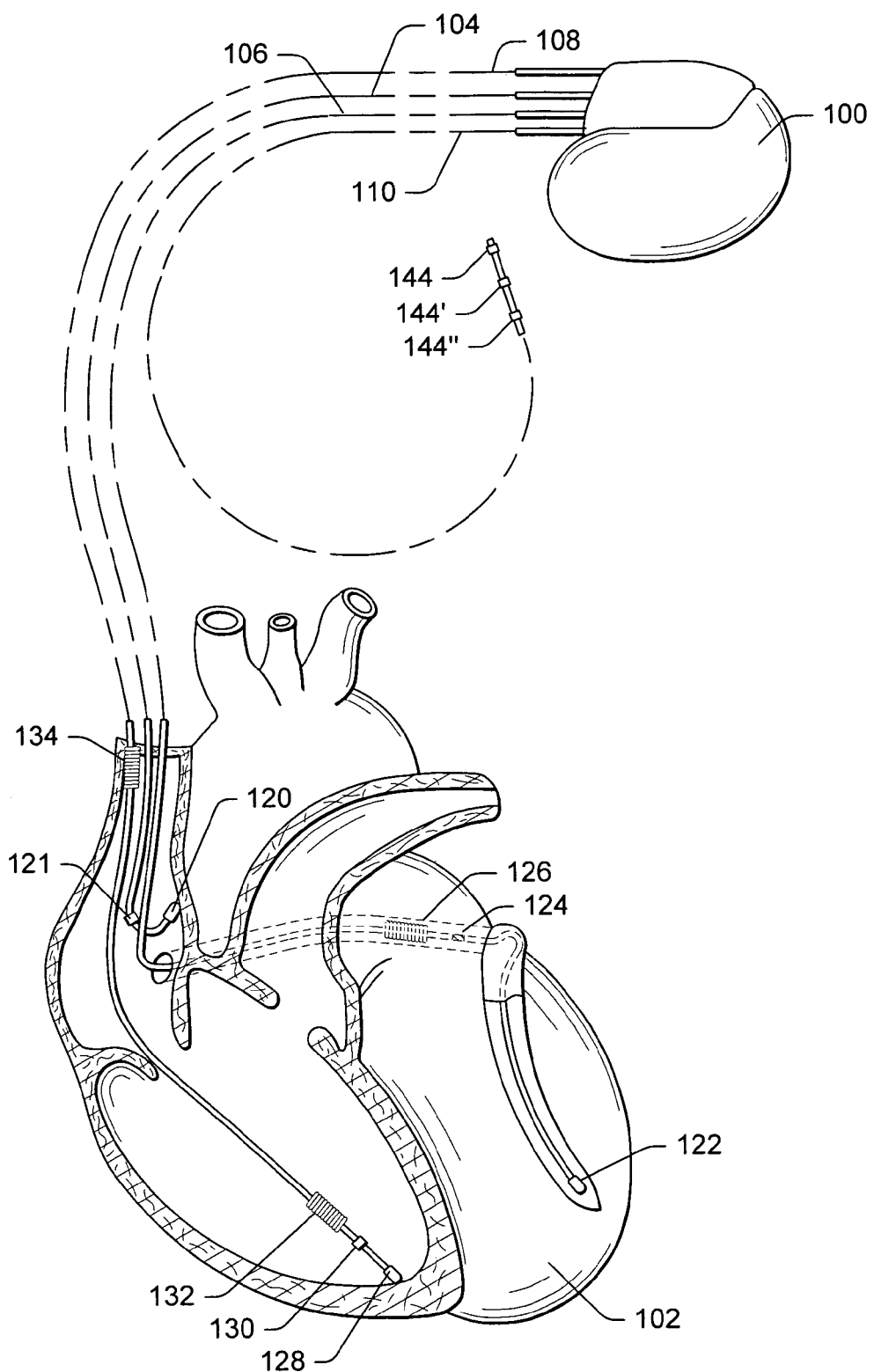
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
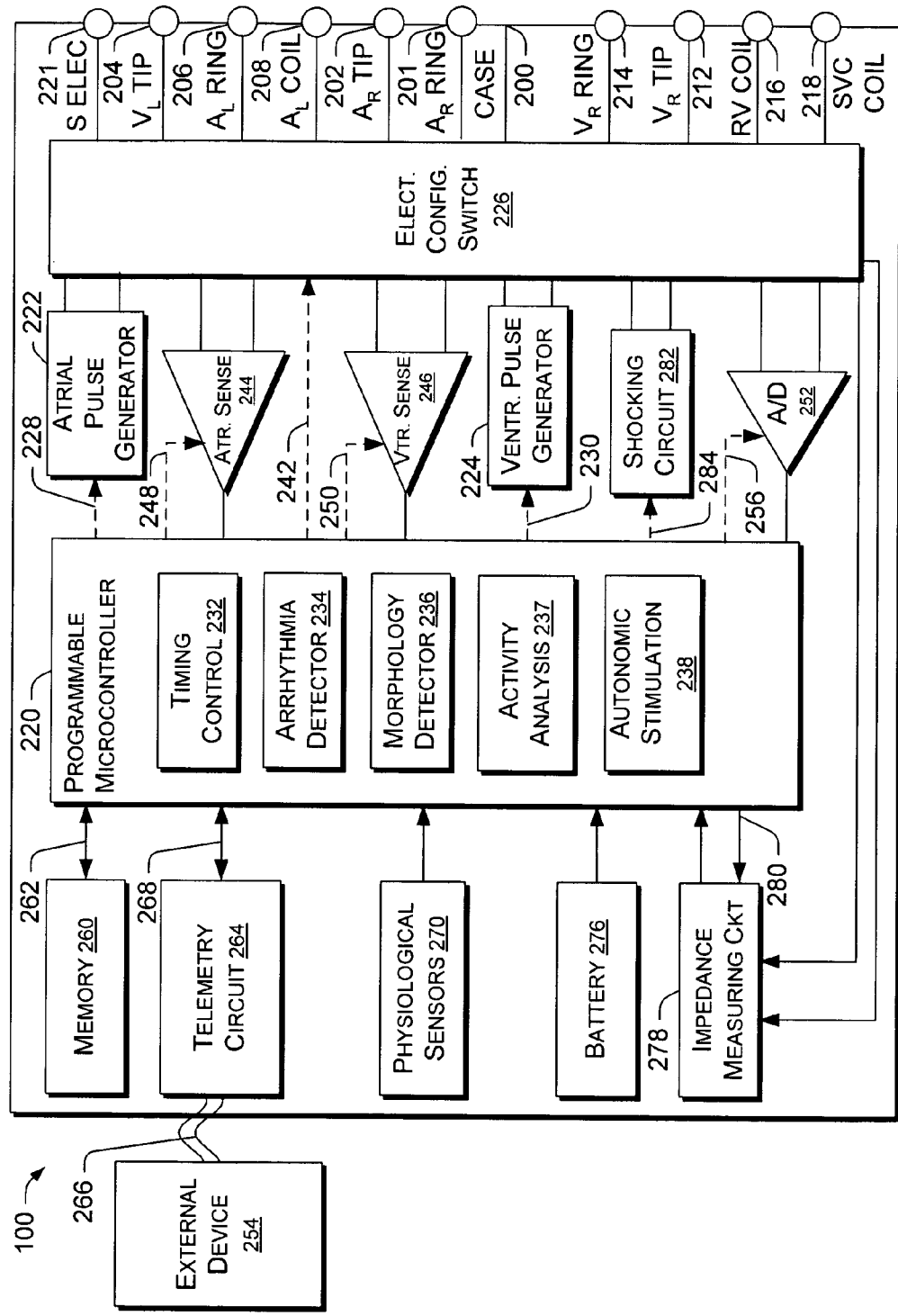
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrioventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an activity analysis module 237. The activity analysis module 237 optionally implements one or more methods for sensing, information analysis, and/or stimulation control related to cardiac activity. For example, the activity analysis module 237 optionally implements one or more of the exemplary methods described below.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, parasympathetic stimulation. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
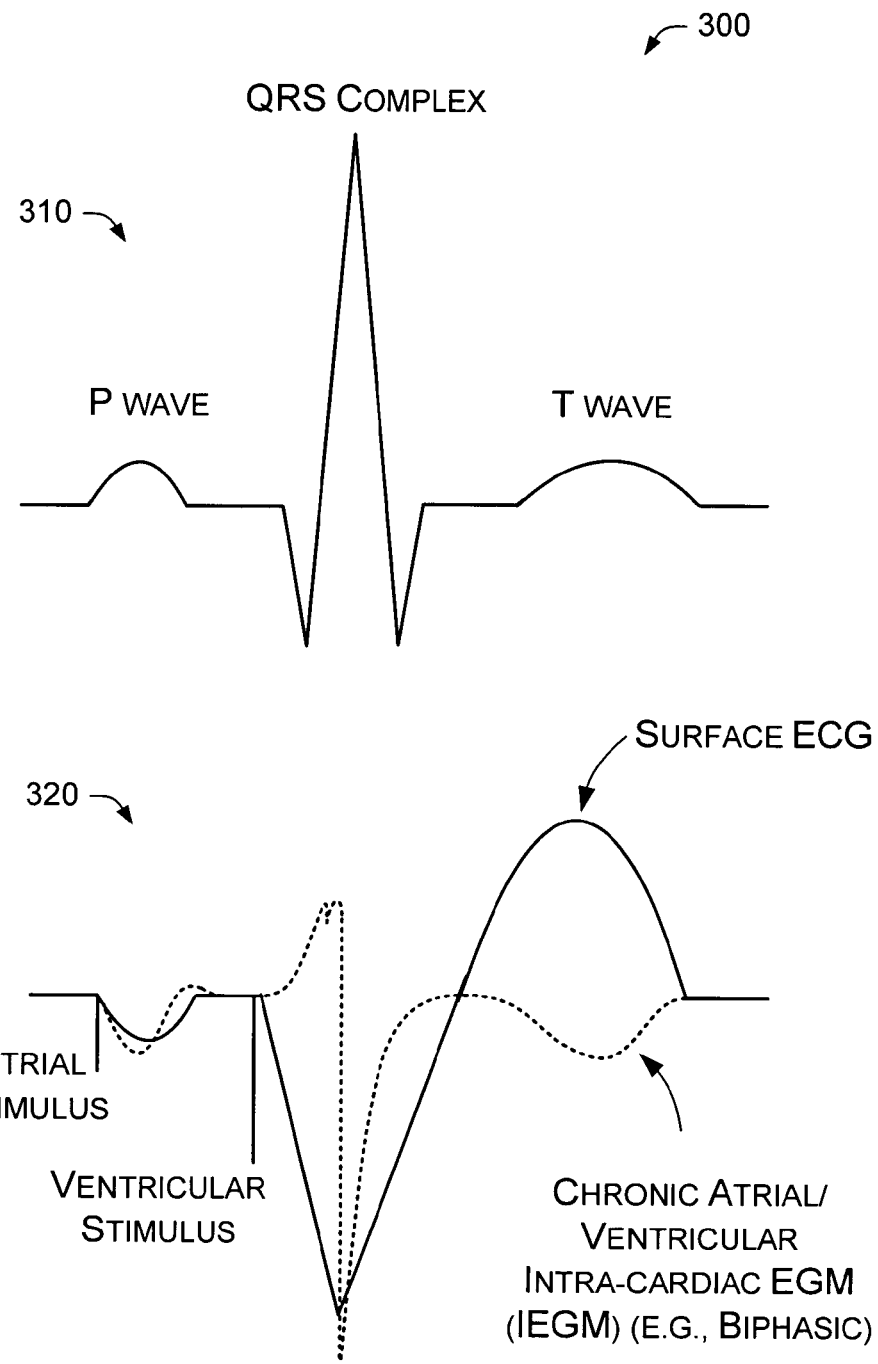
FIG. 3 is a diagram of exemplary waveforms that exhibit cardiac activity responsive to native and/or applied stimuli.

Referring to FIG. 3, exemplary waveforms 300 are shown. The waveforms 300 include an exemplary waveform 310 based on native cardiac activity and an exemplary ECG waveform 320 and an exemplary IEGM waveform 324 based on delivered stimuli. These exemplary waveforms 300 exhibit differences between native activity, paced activity and surface and intra-cardiac sensing. The IEGM 324 is representative of the type of waveform an implantable pacing device may sense. Also note the waveforms 320 and 324 show an atrial stimulus and a ventricular stimulus and no native stimuli; thus, these waveforms do not exhibit fusion and/or pseudofusion.

Figure 4:
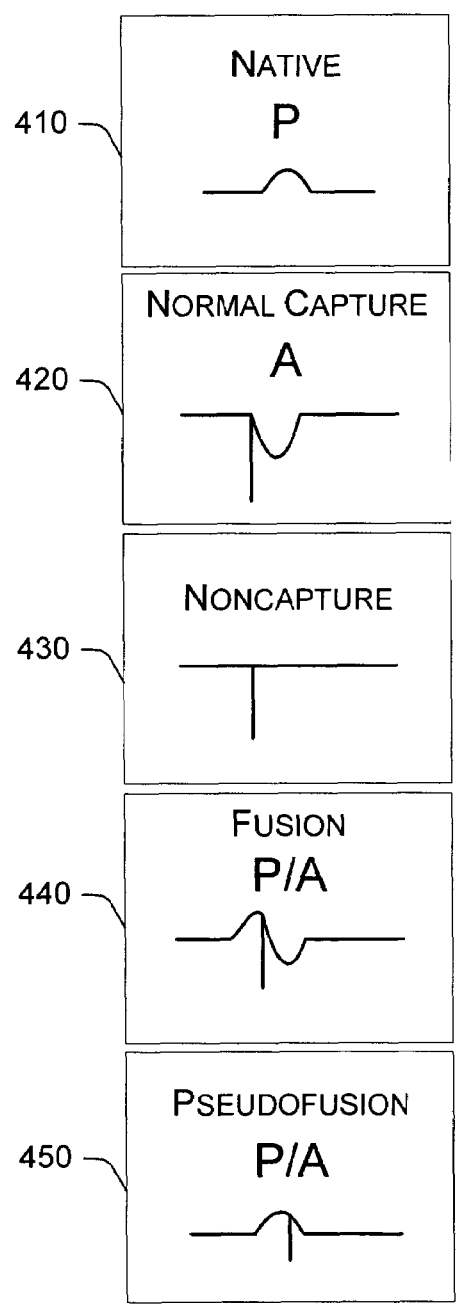
FIG. 4 is a diagram of various exemplary atrial waveforms including native (P wave), capture (A wave), noncapture (with atrial stimulus), atrial fusion (P wave and A wave complex) and atrial pseudofusion (P wave with atrial stimulus).

Referring to FIG. 4, various exemplary atrial waveforms 400 are shown. As discussed herein, an atrial waveform caused by an atrial stimulus is generally referred to as an "A wave" while an atrial waveform caused by a native stimulus (e.g., initiated by the sinoatrial node, etc.) is generally referred to as a "P wave". A native P wave 410 may indicate that a patient does not need atrial pacing. However, if the native rate (e.g., as measured from P wave to P wave), exceeds or falls below a desirable rate, then atrial pacing may be indicated. An A wave 420 indicates that an applied atrial stimulus had sufficient power to "capture" atrial tissue. In comparison to the A wave 420, the noncapture waveform 430, indicates that the applied atrial stimulus did not have sufficient power to sufficiently capture atrial tissue. The last two waveforms 440, 450 exhibit atrial "fusion" and atrial "pseudofusion", respectively.

As mentioned in the Background section, fusion is typically characterized by a wave complex formed by depolarization of the myocardium initiated by both a non-native stimulus and a native stimulus. Thus, atrial fusion is characterized by a wave complex (e.g., the waveform 440) initiated by a native stimulus and a paced atrial stimulus. As mentioned in the Background section, pseudofusion is typically characterized by a wave complex formed by depolarization of the myocardium initiated by a native stimulus; however, a non-native stimulus, that does not significantly contribute to depolarization, is present that distorts the wave complex. Thus, atrial pseudofusion is characterized by a wave complex (e.g., the waveform 450) initiated by a native stimulus and distorted by a paced atrial stimulus. While the exemplary waveforms 400 generally pertain to atrial waveforms, similar waveforms exist that correspond to ventricles.

As demonstrated by these exemplary waveforms 400, for a variety of reasons, pacing devices that aim to detect and/or characterize cardiac activity may misinterpret fusion and/or pseudofusion waveforms as noncapture or loss of capture. Further, a pacing device may not need to implement pacing if a native stimulus is present. Again, in both fusion and pseudofusion (e.g., the waveforms 440, 450), native activity is present.

While the exemplary waveforms 400 generally pertain to atrial waveforms, similar waveforms exist that correspond to ventricles. In the description that follows, waveforms that correspond to ventricular evoked responses (e.g., ventricular capture) and/or atrial evoked responses (e.g., atrial capture) are discussed in more detail with respect to a variety of exemplary methods and/or devices that aim to enhance detection and/or characterization of cardiac activity.

Figure 5:
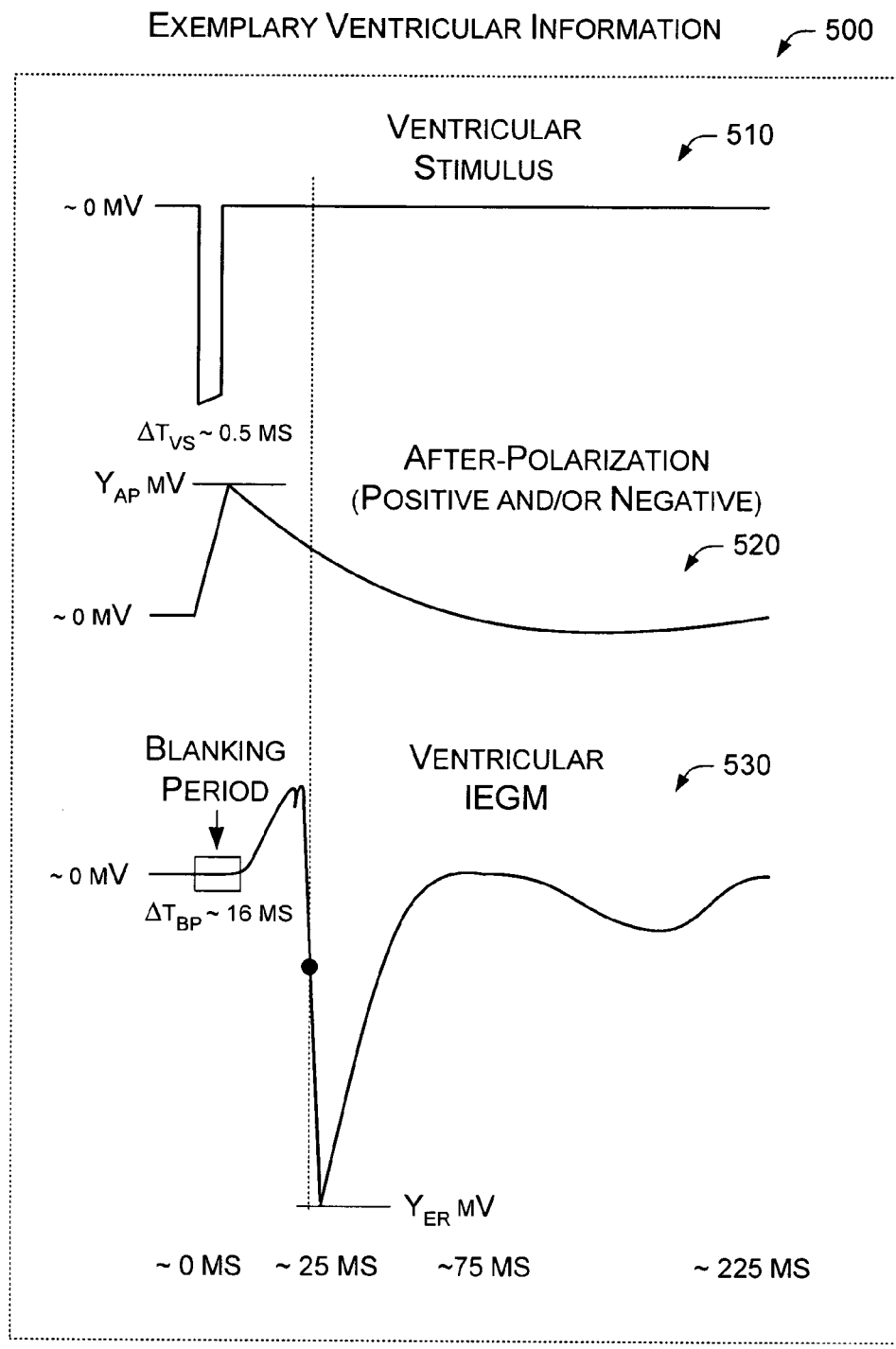
FIG. 5 is a diagram of exemplary ventricular information including a ventricular stimulus, ventricular afterpotential and a ventricular IEGM.

Referring to FIG. 5, exemplary ventricular information 500 is shown. The exemplary ventricular information 500 includes a plot of ventricular stimulus voltage versus time 510, a plot of afterpotential voltage with respect to time 520 and a plot of sensed activity with respect to time 530. The exemplary time scale in the plot 530 illustrates that ventricular activity typically occurs in a post-stimulus time frame of approximately one to several hundred milliseconds. Other events, such as the stimulation pulse width (e.g. $\Box t_{VS}$~0.5 ms) of the plot 510 and/or the afterpotential rise and decay of the plot 520 are also exemplary and may not correspond precisely to the time scale of the plot 530.

The plot 510 exhibits a ventricular stimulus (VS) at approximately 0 ms, wherein the stimulus has a magnitude of Ys mV and a duration of approximately $\Delta t_{VS}$ ms. The corresponding afterpotential plot 520 exhibits a rise to $Y_{AP}$ mV at approximately 0 ms. The ventricular IEGM plot 530 exhibits a ventricular stimulus at approximately 0 ms and a corresponding blanking period (e.g., $\Delta t_{BP}$~16 ms). A blanking period is typically an interval initiated by the delivery of a stimulus during which sensing (e.g., a sense amplifier) is temporarily disabled. In dual-chamber pulse generators, a blanking period may also prevent inappropriate detection of signals from another chamber (e.g., crosstalk). Blanking periods are not available in all pacing devices and the blanking period, typically stated in milliseconds, may be preset or programmable. Note that the afterpotential plot 520 does not include a blanking period; however, if it did, the afterpotential would, for example, rise from the baseline (e.g., 0 mV) at approximately the end of the blanking period, typically to a level less than approximately $Y_{AP}$ mV. Also note that the afterpotential may appear inverse to that shown in FIG. 5, for example, due to sensing polarity, etc.

As shown in FIG. 5, the IEGM in the plot 530 exhibits a minimum voltage, e.g., $Y_{ER}$ mV, near approximately 25 ms. Just prior to this minimum, is a vertical dashed line and a solid dot that indicate one possible evoked response detection point. For example, a derivative-based evoked response detection scheme may detect a maximum negative derivative of voltage versus time at approximately the location of the dashed vertical line. Note, that at this location, a significant nonzero afterpotential voltage exists in the afterpotential plot 520. Thus, afterpotential may affect accuracy of such a derivative-based evoked response detection scheme. In particular, note that while the afterpotential also has a negative slope in the neighborhood of the dashed vertical line, it also has positive amplitude whereas the ventricular IEGM has negative amplitude in the neighborhood of the dashed vertical line due to ventricular depolarization. In instances where the positive amplitude of the afterpotential exceeds the negative amplitude of ventricular depolarization, a ventricular IEGM may actually have positive amplitude. While such a hypothetical ventricular IEGM may, at such a neighborhood, have positive amplitude, it will typically maintain a negative slope. The presence of native activity may further complicate detection and/or characterization of "true" ventricular activity. Thus, as described herein, techniques that account for afterpotential and/or more thoroughly characterize typical evoked responses help in detection and/or characterization of cardiac activity.

In general, ventricular activity differs from atrial activity in that intracardiac ventricular activity typically exhibits greater amplitude than intracardiac atrial activity. Further, the frequency response of intracardiac ventricular evoked responses is usually less than that of intracardiac atrial evoked responses. Yet further, atrial evoked responses typically occur more quickly following an atrial stimulus when compared to ventricular evoked responses following a ventricular stimulus. Thus, for implantable pacing devices that employ atrial pacing and atrial sensing, detection and/or characterization of atrial activity is normally more difficult when compared to detection and/or characterization of ventricular activity. In addition, afterpotentials associated with atrial pacing further complicate detection and/or characterization of atrial activity. Thus, while various exemplary methods and/or devices presented herein optionally apply to ventricular activity, they are particularly suitable for atrial activity. Thus, the description that follows, at times, references various atrial examples, understanding that ventricular analogs may also apply.

Figure 6:
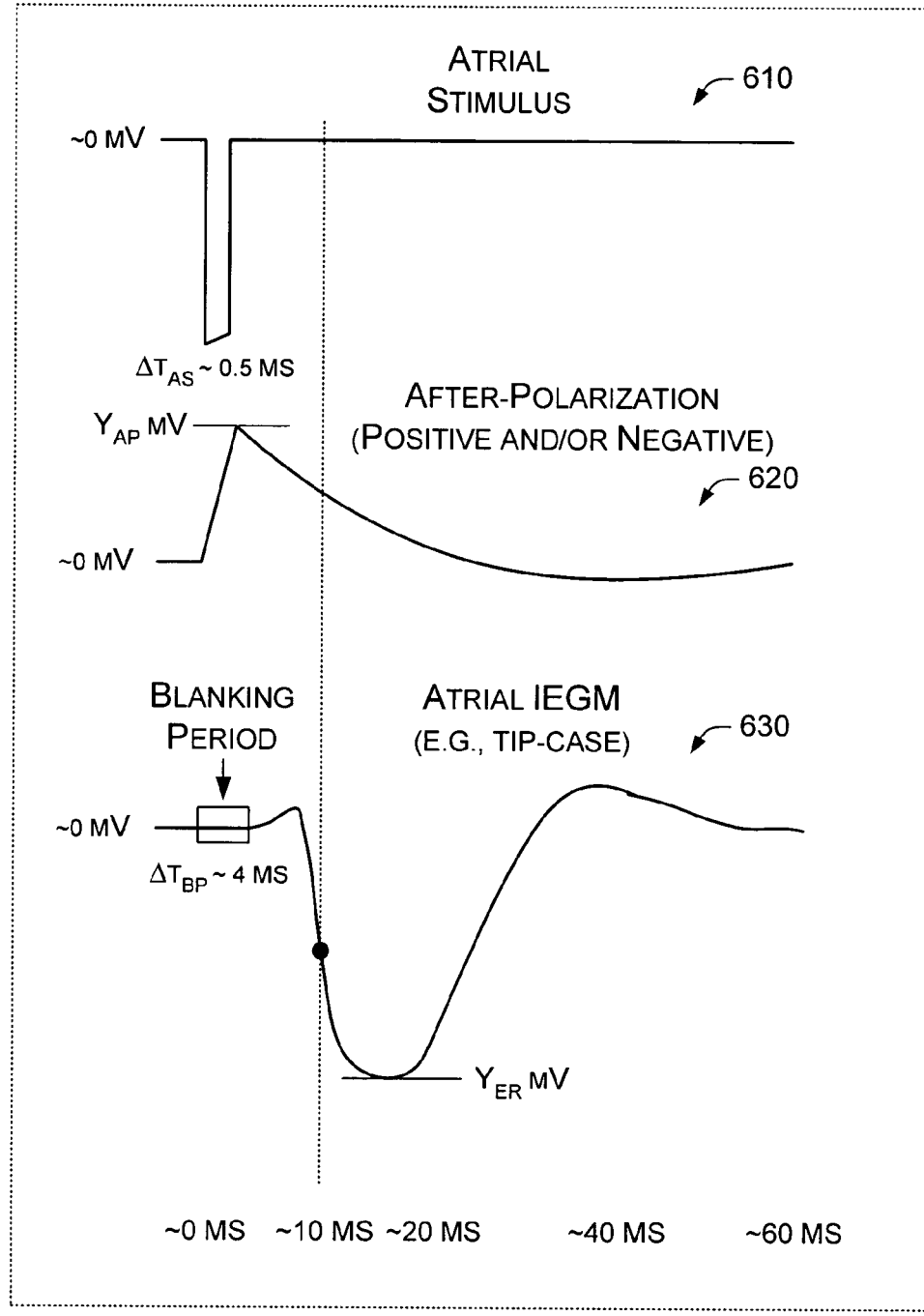
FIG. 6 is a diagram of exemplary atrial information including an atrial stimulus, atrial afterpotential and an atrial IEGM.

Referring to FIG. 6, exemplary atrial information 600 is shown. The exemplary atrial information 600 includes a plot of atrial stimulus voltage versus time 610, a plot of afterpotential voltage with respect to time 620 and a plot of sensed activity with respect to time 630. The exemplary time scale in the plot 630 illustrates that atrial activity typically occurs in a post-stimulus time frame of approximately less than one hundred milliseconds. Other events, such as the stimulation pulse width (e.g., $\Delta t_{AS}$~0.5 ms) of the plot 610 and/or the afterpotential rise and decay of the plot 620 are also exemplary and may not correspond precisely to the time scale of the plot 630.

The plot 610 exhibits an atrial stimulus (AS) at approximately 0 ms, wherein the stimulus has a magnitude of $Y_S$ mV and a duration of approximately $\Delta t_{AS}$ ms. The corresponding afterpotential plot 620 exhibits a rise to $Y_{AP}$ mV at approximately 0 ms. The atrial IEGM plot 630 exhibits an atrial stimulus at approximately 0 ms and a corresponding blanking period (e.g., $\Delta t_{BP}$~4 ms). Note that the afterpotential plot 620 does not include a blanking period; however, if it did, the afterpotential would, for example, rise from the baseline (e.g., 0 mV) at approximately the end of the blanking period, typically to a level less than approximately $Y_{AP}$ mV. Also note that the afterpotential may appear inverse to that shown in FIG. 6, for example, due to sensing polarity, etc.

As shown in FIG. 6, the IEGM in the plot 630 exhibits a minimum voltage, e.g., $Y_{ER}$ mV, at approximately 20 ms. Just prior to this minimum (e.g., at approximately 10 ms), is a vertical dashed line and a solid dot that indicate one possible evoked response detection point. For example, a derivative-based evoked response detection scheme may detect a maximum negative derivative of voltage versus time at approximately the location of the dashed vertical line. Note, that at this location, a significant nonzero afterpotential voltage exists in the afterpotential plot 620. Thus, afterpotential may affect accuracy of such a derivative-based evoked response detection scheme. In particular, note that while the afterpotential also has a negative slope in the neighborhood of the dashed vertical line, it also has positive amplitude whereas the atrial IEGM has negative amplitude in the neighborhood of the dashed vertical line due to atrial depolarization. In instances where the positive amplitude of the afterpotential exceeds the negative amplitude of atrial depolarization, an atrial IEGM may actually have positive amplitude. While such a hypothetical atrial IEGM may, at such a neighborhood, have positive amplitude, it will typically maintain a negative slope. The presence of native activity may further complicate detection and/or characterization of "true" atrial activity. Thus, as described herein, techniques that account for afterpotential and/or more thoroughly characterize typical evoked responses help in detection and/or characterization of cardiac activity.

Ensemble Averaging and/or Other Averaging

In ensemble averaging successive signals are collected and summed typically on a point-by-point or other basis. Therefore, a prerequisite for the application of ensemble averaging is the ability to reproduce a signal enough times to reach a desirable increase in signal to noise. Typical application of ensemble averaging is found in NMR and FT-IR spectroscopy, where the final spectrum is the result of averaging a plurality of individual spectra, which is often necessary to obtain a meaningful signal for cases where a single scan generates a practically unreadable signal heavily contaminated with random noise.

According to ensemble averaging, repetitive additions of noisy signals tend to emphasize their systematic characteristics and to cancel out any zero-mean random noise. If $SNR_o$ is the original signal-to-noise ratio of a signal, the final $SNR_f$ after N repetitions (or scans) is given by the following equation:

| $SNR_f = SNR_o \cdot N^{0.5}$ (1) | |
|---|---|
| N | Increase in SNR |
| 2 | 1.4 |
| 4 | 2 |
| 6 | 2.4 |
| 8 | 2.8 |
| 10 | 3.2 |
| 25 | 5 |
| 100 | 10 |

Therefore, by averaging, for example, 10 (or 100, etc.) signals (e.g., signal data sets) an approximate 3-fold (or a 10-fold) reduction of noise level is achieved. Note that by increasing "N" from 10 to 25, the increase in SNR is approximately the same as increasing "N" from 2 to 10. Thus, the increase in SNR is greater for ensemble averaging the first 10 signals than for the adding the next 15 to the average. For this reason, ensemble averaging is well-suited for use in implantable pacing devices wherein 10 signals are typically easily acquirable in less than approximately 1 minute (e.g., consider a typical heart rate of 60 beats per minute). As discussed herein, such ensemble averaging optionally provides for more robust detection and/or characterization of cardiac activity.

Figure 7A:
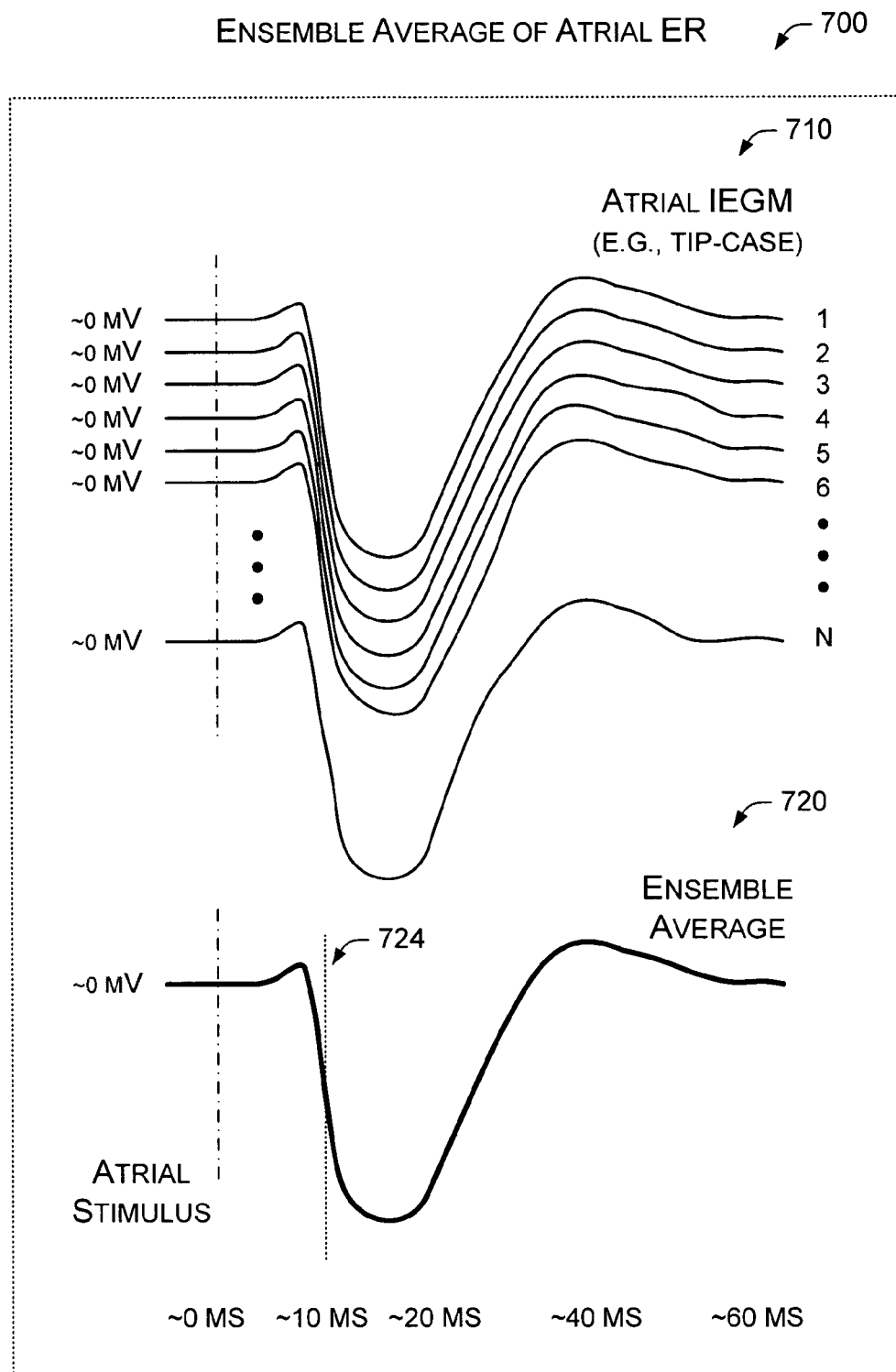
FIG. 7A is a diagram of a series of exemplary atrial IEGMs and an exemplary ensemble average of the series of atrial IEGMs.

Referring to FIG. 7A, an exemplary ensemble average scheme 700 for an atrial evoked response is shown. A series of atrial IEGMs (e.g., 1 to N) 710 are acquired responsive to successive atrial stimuli. In this example, the atrial stimuli are optionally delivered at a fixed rate and/or a variable rate that optionally depends on occurrence (or nonoccurrence) of another event. These individual atrial IEGMs 710 are then ensemble averaged to produce an ensemble average atrial IEGM 720. Of course, a criterion or criteria (e.g., standard deviation, etc.) are optionally used to exclude certain individual atrial IEGMs, for example, a noncapture atrial IEGM is optionally excludable. While variability between atrial IEGMs may exceed variability between NMR scans, in general, an increase in SNR will be realized that can be approximated by Equation 1, above.

The ensemble average atrial IEGM 720 exhibits a vertical line at approximately 20 ms, which corresponds to a region wherein a derivative-based scheme may detect an atrial evoked response. In general, an ensemble average of atrial evoked responses (IEGM) may provide a base derivative value, a "window" and/or other information to aid in detection and/or characterization of atrial activity. Of course, a variety of other features exist within the ensemble average IEGM 720, which are optionally suitable for such purpose. Alternatively, or in addition to, the entire ensemble average (e.g., from approximately 5 ms or less to approximately 60 ms or more) is optionally suitable for use in detection and/or characterization of atrial activity. Note that, as described below, timing and/or features may differ for a ventricular ensemble average (e.g., a window starting at approximately 15 ms or more and extending beyond a time of 60 ms may be appropriate for a ventricular ensemble average).

Figure 7B:
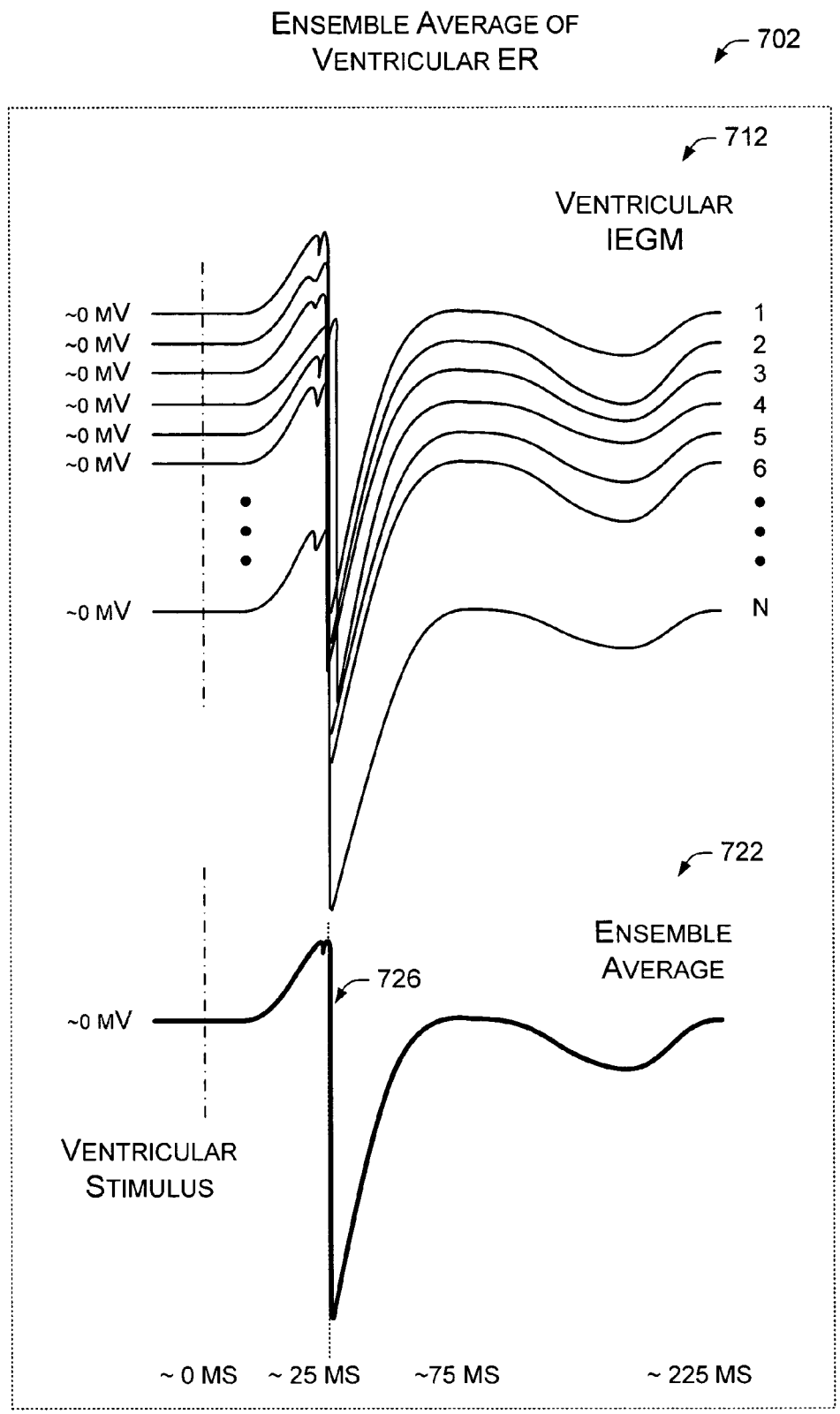
FIG. 7B is a diagram of a series of exemplary ventricular IEGMs and an exemplary ensemble average of the series of ventricular IEGMs.

FIG. 7B shows an exemplary ensemble average scheme 702 for a ventricular evoked response is shown. A series of atrial IEGMs (e.g., 1 to N) 712 are acquired responsive to successive atrial stimuli. In this example, the ventricular stimuli are optionally delivered at a fixed rate and/or a variable rate that optionally depends on occurrence (or nonoccurrence) of another event. These individual ventricular IEGMs 712 are then ensemble averaged to produce an ensemble average atrial IEGM 722. Of course, a criterion or criteria (e.g., standard deviation, etc.) are optionally used to exclude certain individual ventricular IEGMs, for example, a noncapture ventricular IEGM is optionally excludable. While variability between ventricular IEGMs may exceed variability between NMR scans, in general, an increase in SNR will be realized that can be approximated by Equation 1, above.

The ensemble average ventricular IEGM 722 exhibits a vertical line at approximately 25 ms, which corresponds to a region wherein a derivative-based scheme may detect a ventricular evoked response. In general, an ensemble average of ventricular evoked responses (IEGM) may provide a base derivative value, a "window" and/or other information to aid in detection and/or characterization of atrial activity. Of course, a variety of other features exist within the ensemble average IEGM 722, which are optionally suitable for such purpose. Alternatively, or in addition to, the entire ensemble average (e.g., from approximately 15 ms or less to approximately 60 ms or more) is optionally suitable for use in detection and/or characterization of ventricular activity.

Figure 8:
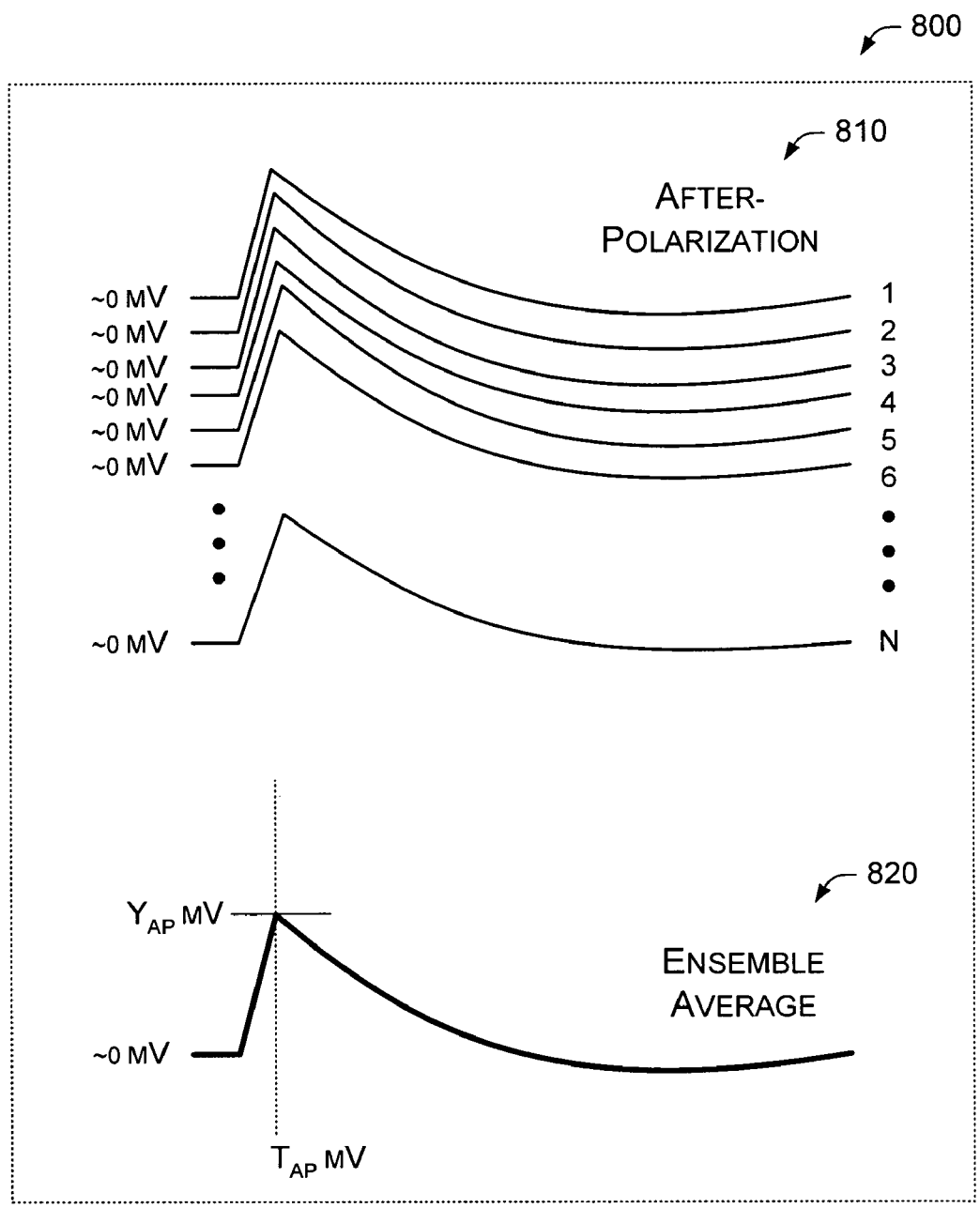
FIG. 8 is a diagram of a series of exemplary afterpotentials (e.g., atrial and/or ventricular) and an exemplary ensemble average of the series of afterpotential IEGMs.

Recognizing that the exemplary ensemble average 720 of FIG. 7A or the exemplary ensemble average 722 of FIG. 7B may contain afterpotential artifact, because afterpotential is typically not "random" noise, in some instances, analysis of afterpotential is optionally appropriate. Referring to FIG. 8, an exemplary ensemble average scheme 800 for afterpotential is shown. A series (e.g., 1 to N) of afterpotential responses (e.g., IEGMs) 810 are acquired responsive to successive sub-threshold stimuli and/or stimuli delivered during a refractory period.

In this example, the stimuli are optionally delivered at a fixed rate and/or a variable rate that optionally depends on occurrence (or nonoccurrence) of another event. These individual responses 810 are then ensemble averaged to produce an ensemble average afterpotential response 820. Of course, a criterion or criteria (e.g., standard deviation, etc.) are optionally used to exclude certain individual afterpotential responses, for example, a capture IEGM is optionally excludable. While variability between IEGMs may exceed variability between NMR scans, in general, an increase in SNR will be realized that can be approximated by Equation 1, above.

The ensemble average afterpotential IEGM 820 exhibits a vertical line at approximately $t_{AP}$ ms, which corresponds to a region wherein a scheme may detect a maximum afterpotential. In general, an ensemble average of afterpotential responses (IEGM) may be used to extract afterpotential artifact from an atrial and/or a ventricular IEGM (e.g., individual and/or ensemble average). In addition, as described in more detail below, one or more ensemble averages are optionally acquired at different stimulus power levels.

Figure 9:
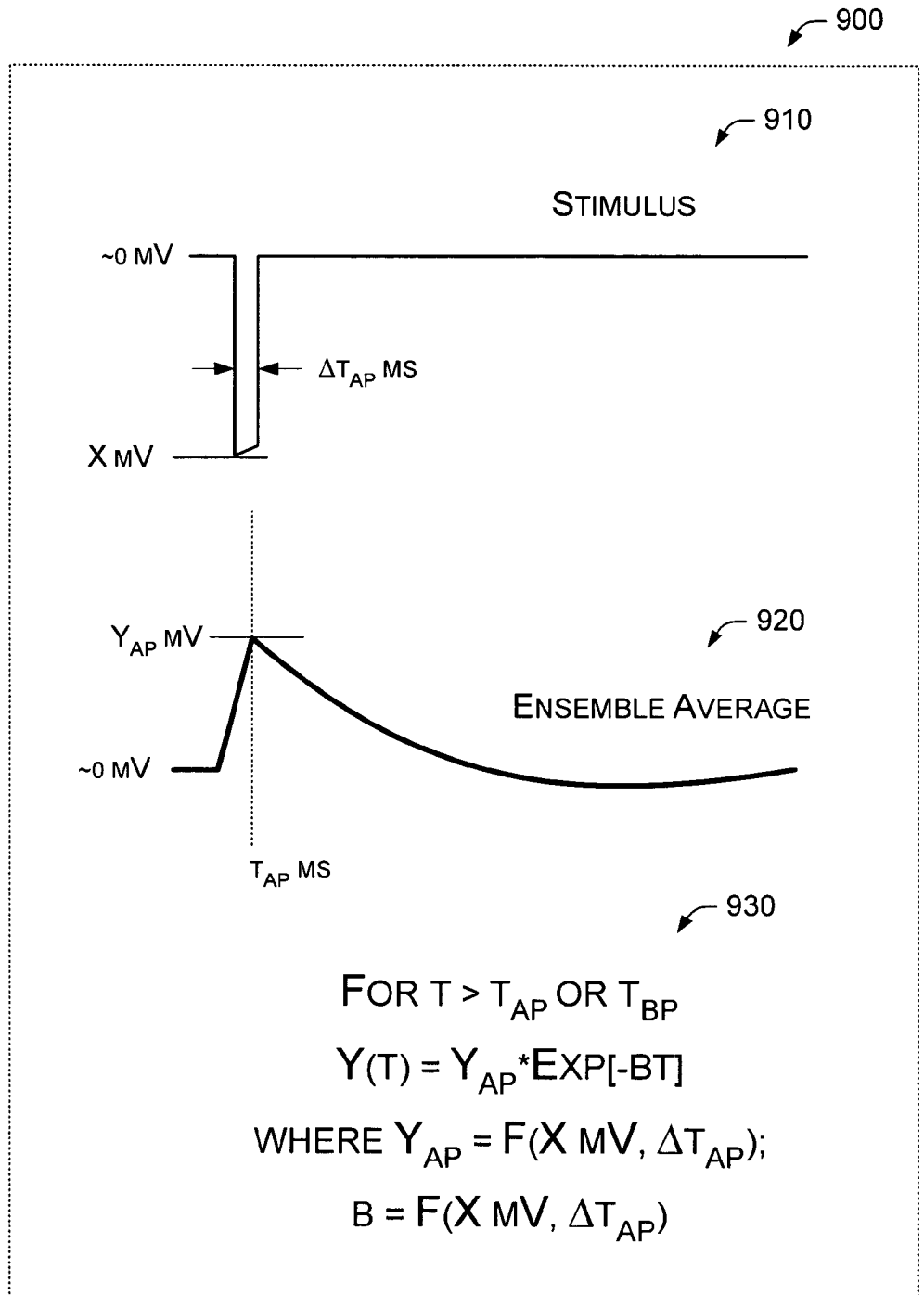
FIG. 9 is a diagram of an exemplary stimulus, exemplary afterpotential and exemplary equations for analysis.

Referring to FIG. 9, exemplary analyses 900 of afterpotential information are shown. An exemplary stimulus 910 with respect to time includes a stimulus having a maximum amplitude of X mV and duration of Δt ms. An exemplary ensemble average 920 includes a maximum amplitude $Y_{AP}$ mV at a time of approximately $t_{AP}$ ms. Various exemplary equations 930 are also shown which are optionally suitable to analyze afterpotential information. For example, the exemplary ensemble average afterpotential 920 decays substantially exponentially from the time $t_{AP}$ onward. Thus, Equation 2, below, is optionally suitable to model the ensemble average 920:

$$Y(t) = Y_{AP} \text{EXP}[-bt] \quad (2),$$

wherein b is a time constant (e.g., function of X, Δt, etc.) and $Y_{AP}$ is optionally a function of stimulus parameters (e.g., X, Δt, etc.). Through use of such an equation, information contained in the afterpotential ensemble average 920 is reduced to a few parameters (e.g., $Y_{AP}$ and b) which may depend on a few variables (e.g., X, Δt, etc.).

Figure 10:
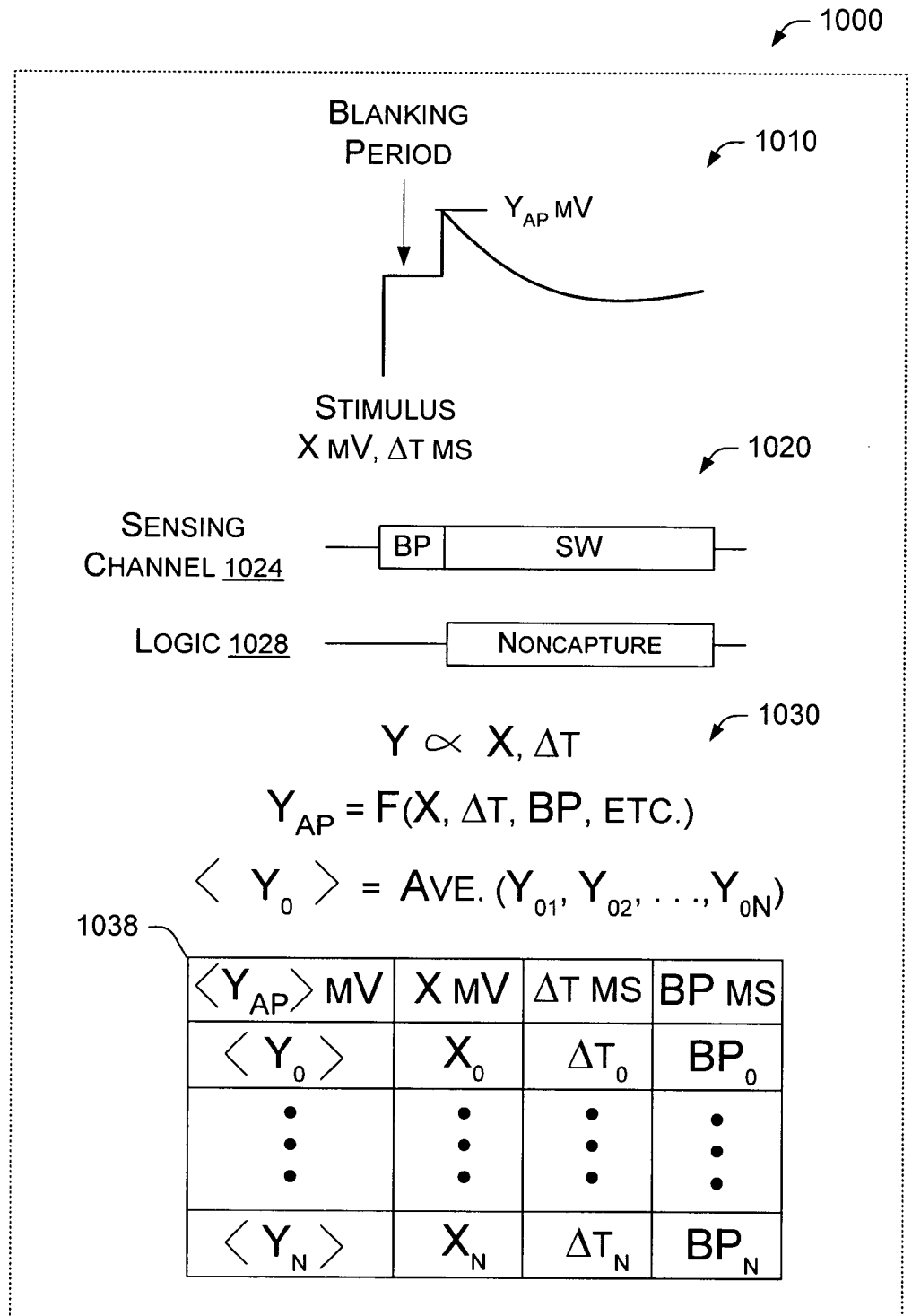
FIG. 10 is a diagram of an exemplary afterpotential, exemplary channels, and exemplary equations and/or tables for analysis.

Referring to FIG. 10, further acquisition and/or analyses 1000 for afterpotential information are shown. An IEGM 1010, which exhibits an afterpotential response, includes a blanking period that begins at approximately the time of stimulus delivery wherein the sensed afterpotential voltage remains at and/or near a base value and after which the value rises to $Y_{AP}$ mV. Sensing channel 1024 includes the blanking period (BP) followed by a sensing window (SW). A logic line 1028 affirms that the stimulus did not result in capture. Various analyses 1030 for the sensed afterpotential information are also shown. In this example, afterpotential is assumed proportional to stimulus amplitude (e.g., X) and duration (e.g., Δt), which is typically the case for intracardiac pacing and sensing. The maximum sensed afterpotential (e.g., which typically occurs at approximately the end of the blanking period), YAP is assumed a function of stimulus amplitude (e.g., X), duration (e.g., Δt), blanking period (e.g., BP), etc.

According to ensemble averaging, an ensemble average of an IEGM is typically an average of a set of IEGMs for a given stimulus power level, etc. Such information is optionally reduced to an equation (or model) or a table, such as, but not limited to, the table 1038. For example, the table 1038 includes a variety of ensemble averages that correspond to system parameters (e.g., X, Δt, BP, etc.). An implantable pacing device optionally stores such information in the form of a table and/or a model (with parameters as applicable).

Figure 11:
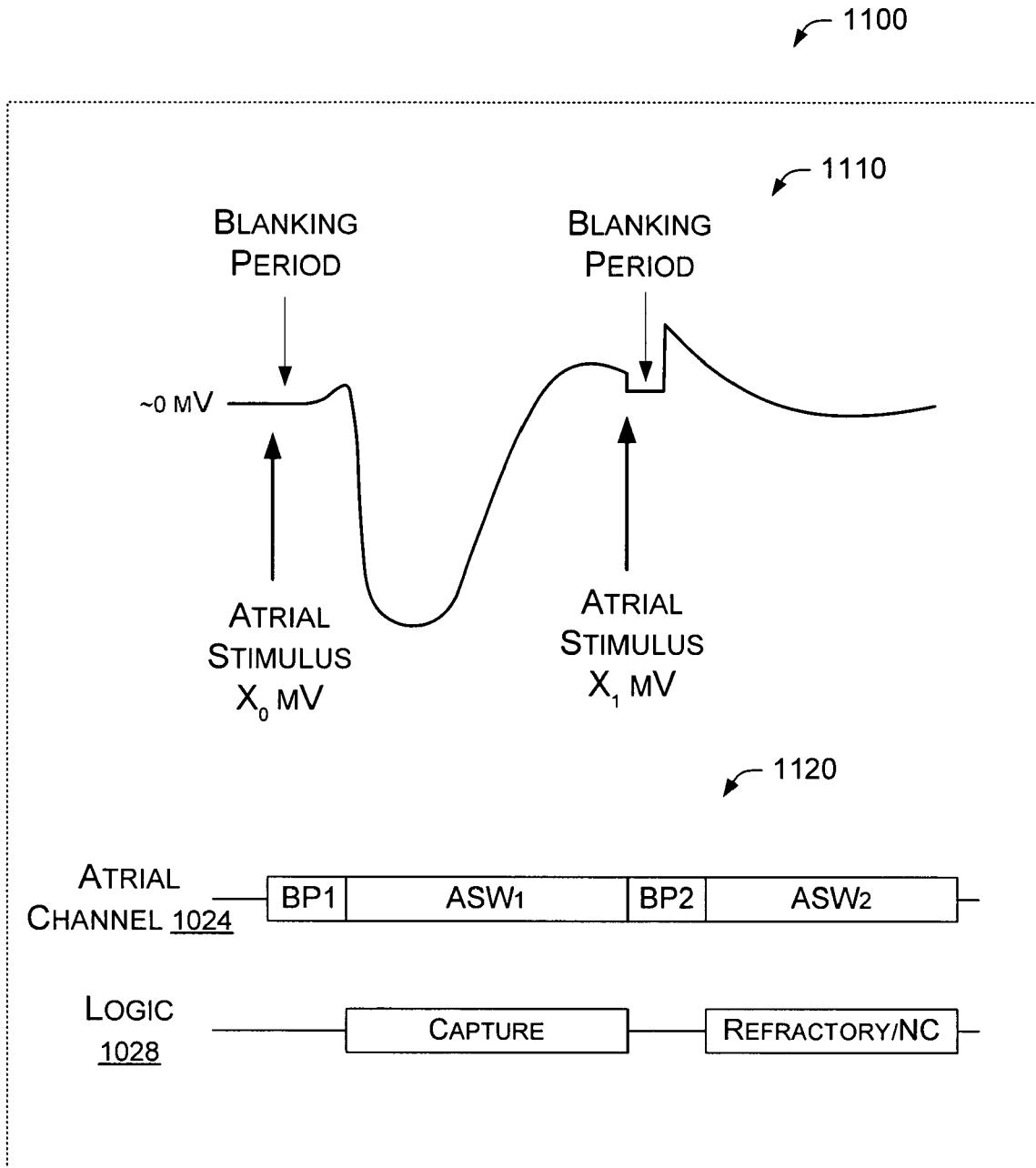
FIG. 11 is a diagram of an exemplary acquisition scheme for acquisition of atrial information including an atrial IEGM and atrial channels.

Referring to FIG. 11, an exemplary method 1100 for acquisition of an evoked response and afterpotential is shown. An exemplary waveform 1110 exhibits an atrial stimulus ($X_0$) followed by a blanking period and an atrial evoked response. Near the end of the evoked response, and, for example while the tissue proximate to the stimulus electrode(s) is still refractory, another stimulus ($X_1$) of the same and/or different power is delivered. Alternatively, a sub-threshold stimulus is delivered. Following the second atrial stimulus ($X_1$), a second blanking period optionally follows, which may differ from the first blanking period, which results in the afterpotential related to the second atrial stimulus ($X_1$). An atrial channel 1024 also shows these events as blanking period 1 (BP1), atrial sensing window 1 (ASW1), blanking period 2 (BP2) and atrial sensing window 2 (ASW2). Of course, the duration of these various periods and/or windows may vary and/or be discontinuous in that they do not occur precisely back-to-back as shown. A logic line 1028 shows logic corresponding to the IEGM 1110 and the atrial channel 1024. For example, the logic 1024 indicates capture based on ASW1 and indicates refractory state, noncapture (NC), afterpotential only during ASW2.

In analyzing information acquired as shown in FIG. 11, an implantable pacing device optionally subtracts the afterpotential from a prior acquired IEGM that includes an afterpotential artifact to produce an artifact removed result on a beat-by-beat and/or other basis. One or more artifact removed results are optionally ensemble averaged.

Figure 12:
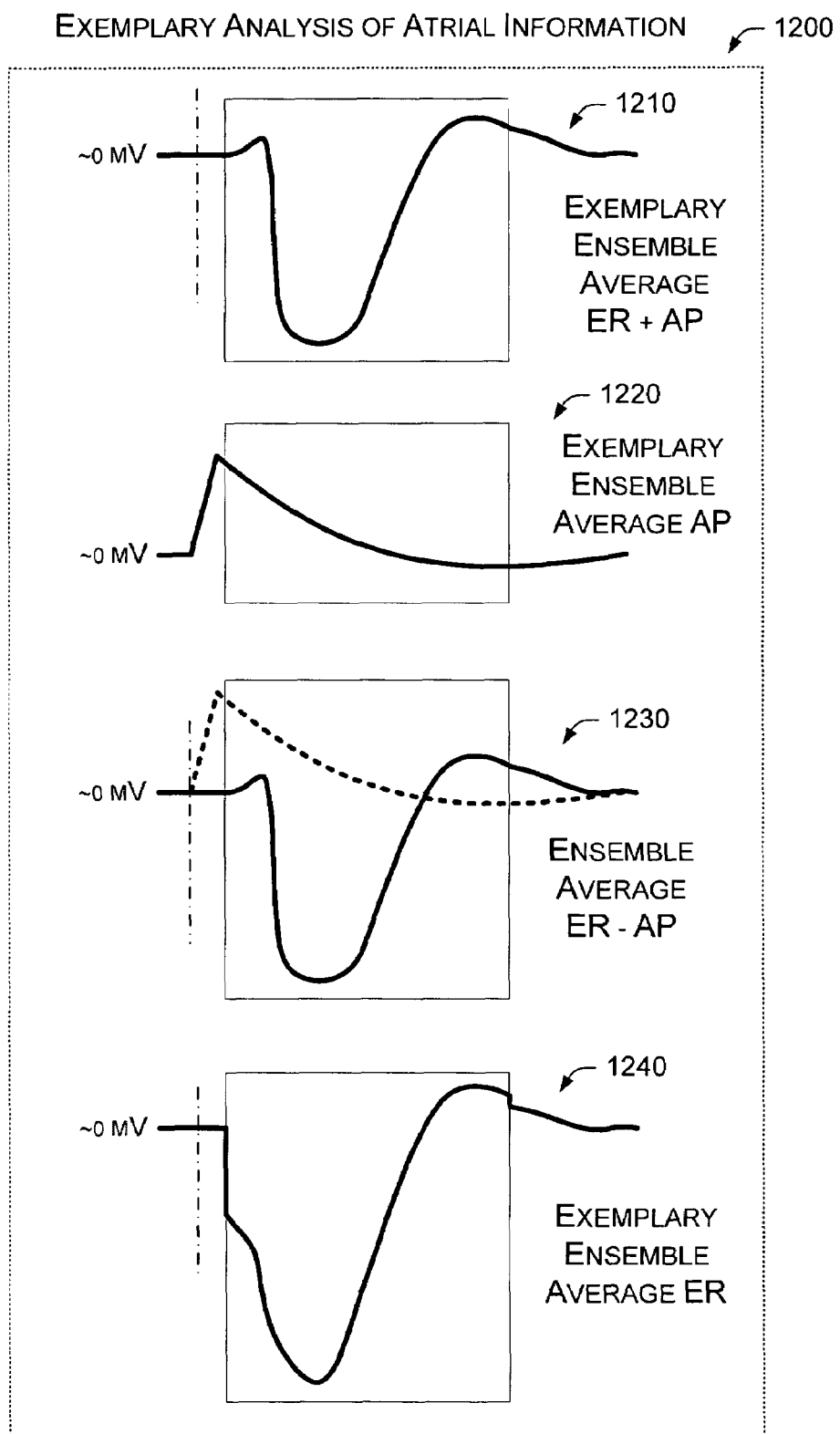
FIG. 12 is a diagram of exemplary waveforms wherein ensemble averaging is implemented for analysis.

Referring to FIG. 12, various exemplary waveforms 1200 are shown. The waveform 1210 includes an evoked response and afterpotential artifact. The exemplary waveform 1220 includes afterpotential artifact, for example, sensed sub-threshold and/or in a refractory period. The exemplary waveform 1230 includes a superposition of the evoked response and afterpotential artifact waveform 1210 and the afterpotential waveform 1220. Subtraction of the afterpotential waveform 1220 from the waveform 1210 results in a "true" evoked response waveform 1240. The various waveforms 1210, 1220, 1240, as shown, optionally include one-dimensional and/or two dimensional windows, which may be used to narrow a waveform to one or more specific regions of interest. Window selection is optionally based on waveform (e.g., signal) amplitude, timing, and/or other factors.

In general, an evoked response, in the case of capture, exhibits little variability with respect to suprathreshold stimulus power; whereas, afterpotential is known to vary with respect to stimulus power. Thus, according to various exemplary methods and/or devices described herein, a stimulus power dependent afterpotential (e.g., the waveform 1220) is subtracted from an ensemble average IEGM (e.g., the waveform 1210) and the result (e.g., the waveform 1240) is compared to a known ensemble average evoked response, which has already had afterpotential artifact removed and/or was acquired using techniques (circuitry, algorithms, etc.) to remove afterpotential artifact. Of course, the result (e.g., the waveform 1240) is optionally analyzed according to another technique in addition to, or in lieu of, comparison to a known ensemble average waveform (e.g., derivative, integral, etc.).

Figure 13:
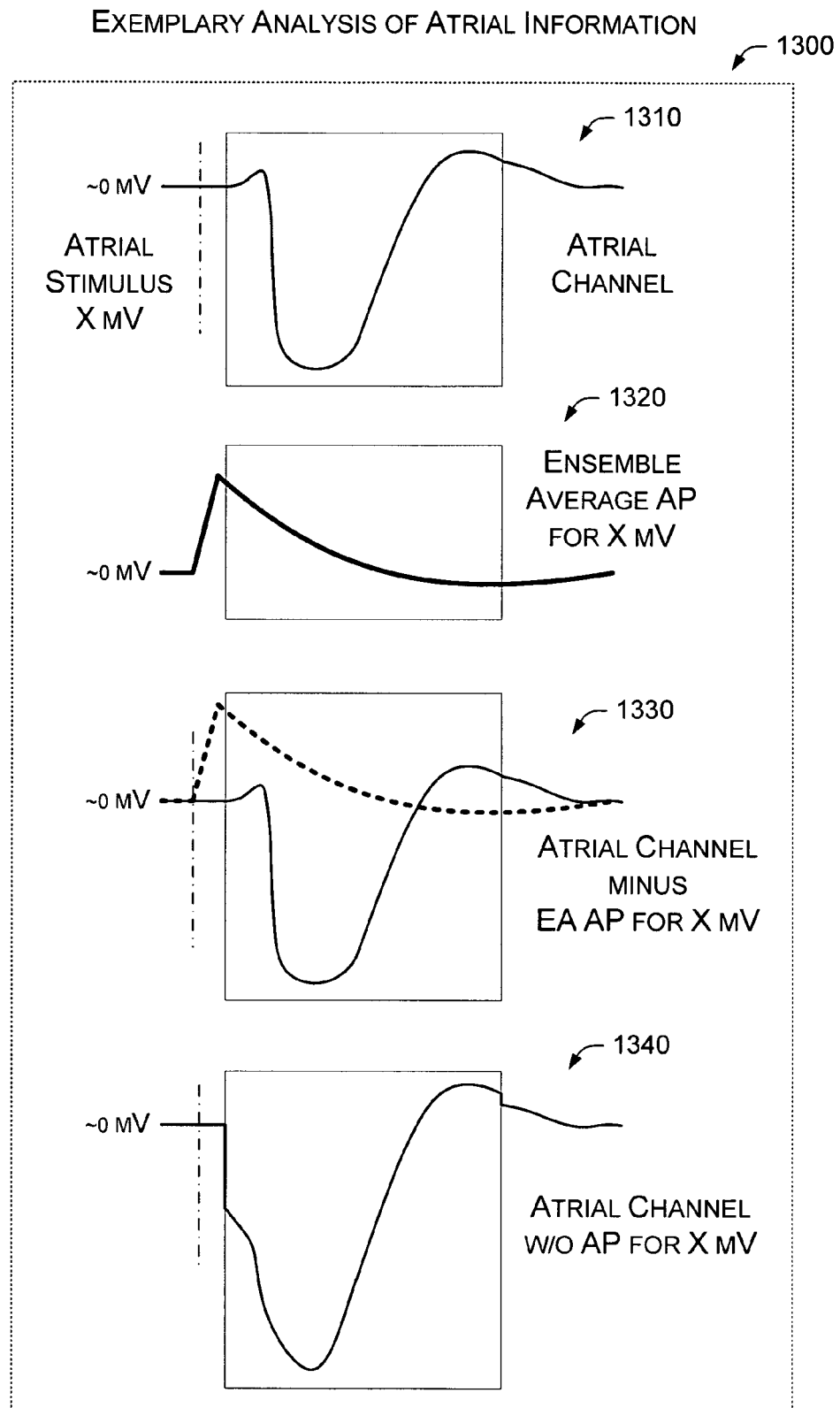
FIG. 13 is a diagram of exemplary waveforms wherein ensemble averaging is implemented for analysis.

Referring to FIG. 13, various exemplary waveforms 1300 (e.g., 1310-1340) are shown wherein a stimulus power dependent afterpotential (e.g., the waveform 1320) is subtracted from an individual ensemble average IEGM (e.g., the waveform 1310) to produce a result (e.g., the waveform 1340). According to various exemplary methods and/or devices described herein, such a result is compared to a known ensemble average evoked response, which has already had afterpotential artifact removed and/or was acquired using techniques (circuitry, algorithms, etc.) to remove afterpotential artifact. Of course, the result (e.g., the waveform 1340) is optionally analyzed according to another technique in addition to, or in lieu of, comparison to a known ensemble average waveform (e.g., derivative, integral, etc.).

Figure 14:
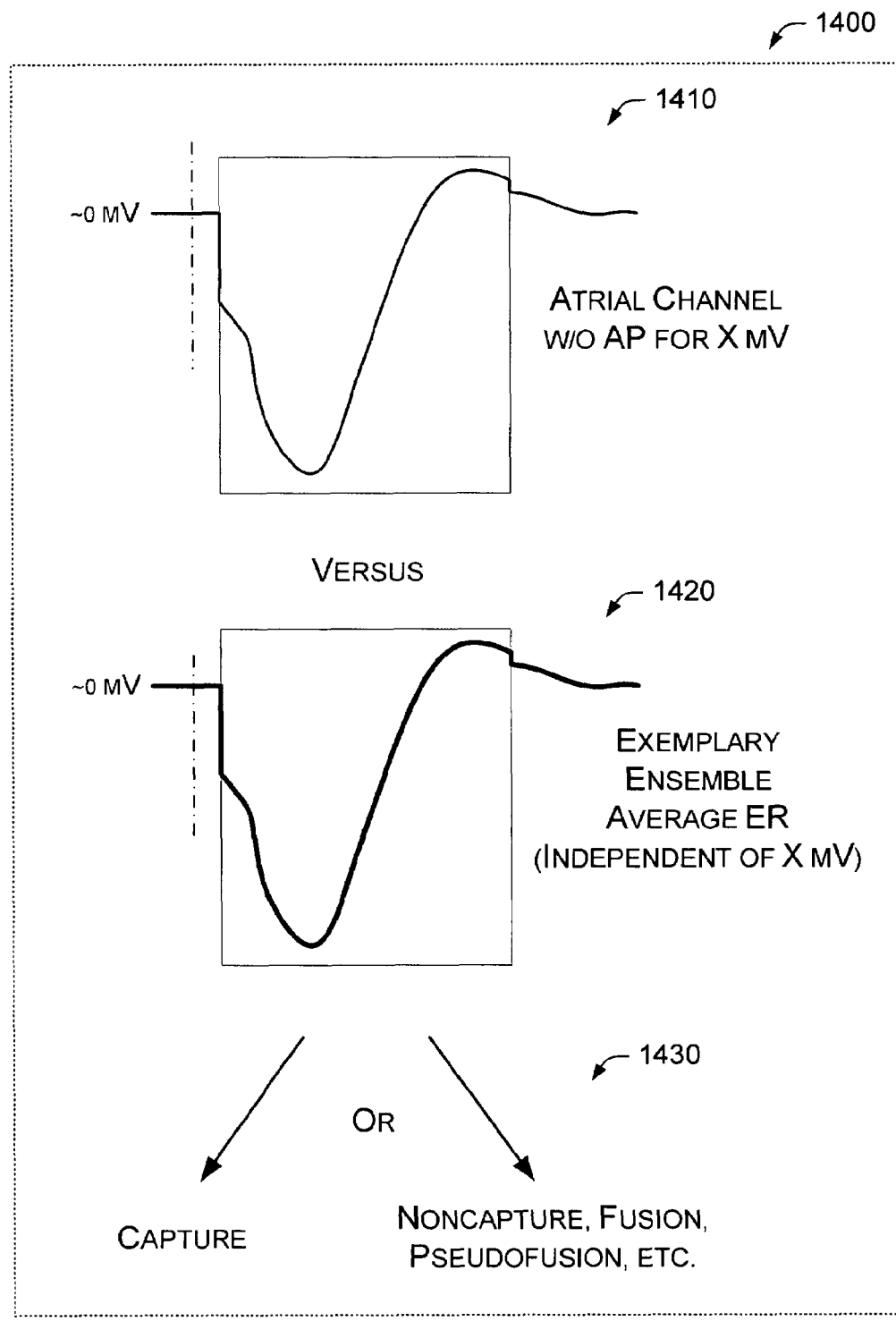
FIG. 14 is a diagram of exemplary waveforms wherein ensemble averaging is implemented for analysis.

Referring to FIG. 14, an exemplary scheme 1400 for analyzing IEGM information is shown. This scheme 1400 involves comparing an atrial IEGM 1410 that has had afterpotential artifact removed to an ensemble average evoked response 1420 (e.g., without afterpotential artifact and hence "independent" of stimulus power) to determine using logic 1430 whether the atrial IEGM indicates capture, noncapture, fusion, pseudofusion, native activity, etc.

Figure 15:
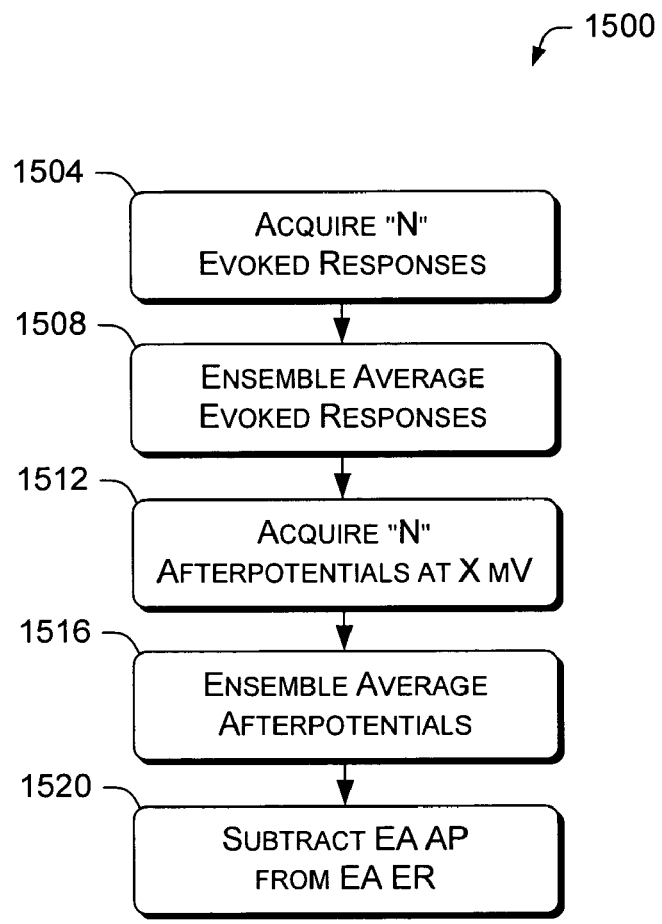
FIG. 15 is a block diagram of an exemplary method for acquiring information for an ensemble average.

Referring to FIG. 15, an exemplary method 1500 for acquiring information is shown. In an acquisition block 1504, an implantable pacing device acquires $N_0$ evoked responses (e.g., IEGMs). Next, in an ensemble average block 1508, the device determines an ensemble average of the $N_0$ evoked responses. Of course, such a block optionally operates simultaneous with the acquisition block 1504 wherein an average is determined on an evoked response-by-evoked response basis. In another acquisition block 1512, the device acquires $N_1$ afterpotentials, for example, at a stimulus amplitude of X mV (e.g. duration $\Delta t$, etc.). Of course, per FIG. 11, acquisition of an evoked response and an afterpotential optionally occurs on a beat-by-beat basis. Next, in another ensemble average block 1516, the device determines an ensemble average of the $N_1$ afterpotentials. Of course, such a block optionally operates simultaneous with the acquisition block 1512 wherein an average is determined on an afterpotential-by-afterpotential basis. In a subtraction block 1520, the device subtracts the ensemble average afterpotential from the ensemble average evoked response. The result is optionally used to serve as information to determine whether any particular IEGM and/or ensemble average IEGM is indicative of capture, noncapture, fusion, pseudofusion, and/or native activity.

Figure 16:
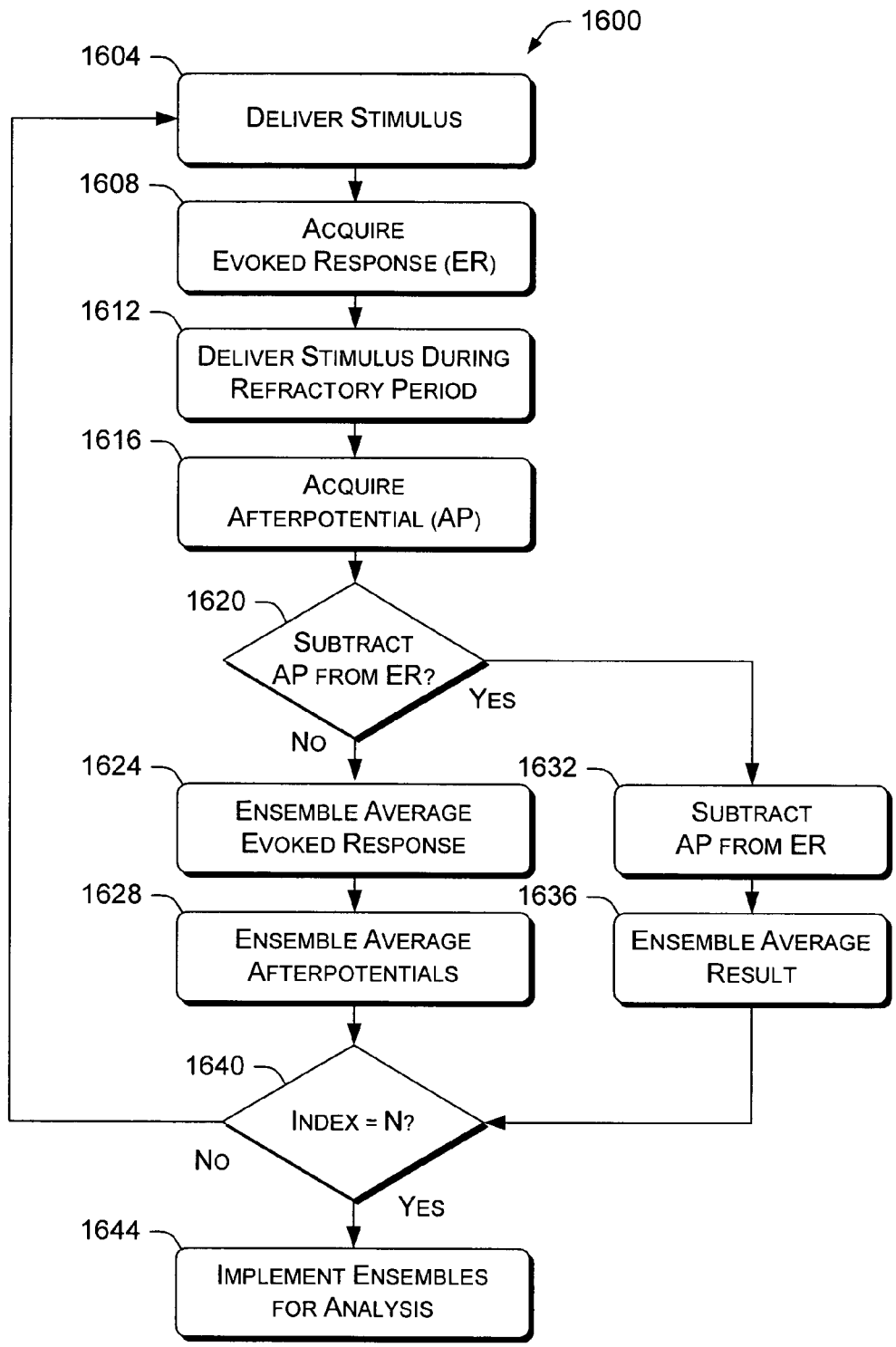
FIG. 16 is a block diagram of an exemplary method for ensemble averaging.

While various exemplary methods for acquiring information have been mentioned above, FIG. 16 shows various blocks associated with an exemplary method 1600 for acquiring information. In a delivery block 1604, an implantable pacing device delivers a stimulus. In an acquisition block 1608, the device senses cardiac activity (e.g., an evoked response, etc.). In another delivery block 1612, the device delivers another stimulus during a refractory period (which typically will not result in an evoked response). In yet another acquisition block 1616, the device senses the afterpotential following the stimulus. Next, in a decision block 1620, the method decides whether to subtract the afterpotential from the evoked response (in general, evoked response will include an afterpotential artifact unless otherwise noted). If the decision block 1620 decides to subtract the acquired afterpotential from the acquired evoked response, then a subtraction block 1632 performs the subtraction. Thereafter, an ensemble average block 1636 performs an ensemble average of the result and the method continues at another decision block 1640 which determines whether N acquisitions have occurred. Again, N is an integer, typically greater than approximately 5, and, in some instances, may differ for the evoked response and afterpotential.

In the case that the decision block 1620 decides not to subtract the afterpotential from the evoked response, then in one ensemble average block 1624, the method 1600 ensemble averages the evoked responses and in another ensemble average block 1628, the method 1600 ensemble averages the afterpotentials. Next, the decision block 1640 determines whether N acquisitions have occurred. If the decision block 1640 determines that N acquisitions have not occurred, then the method 1600 continues at the deliver block 1604. Otherwise, the method 1600 continues at the implementation block 1644.

Figure 17:
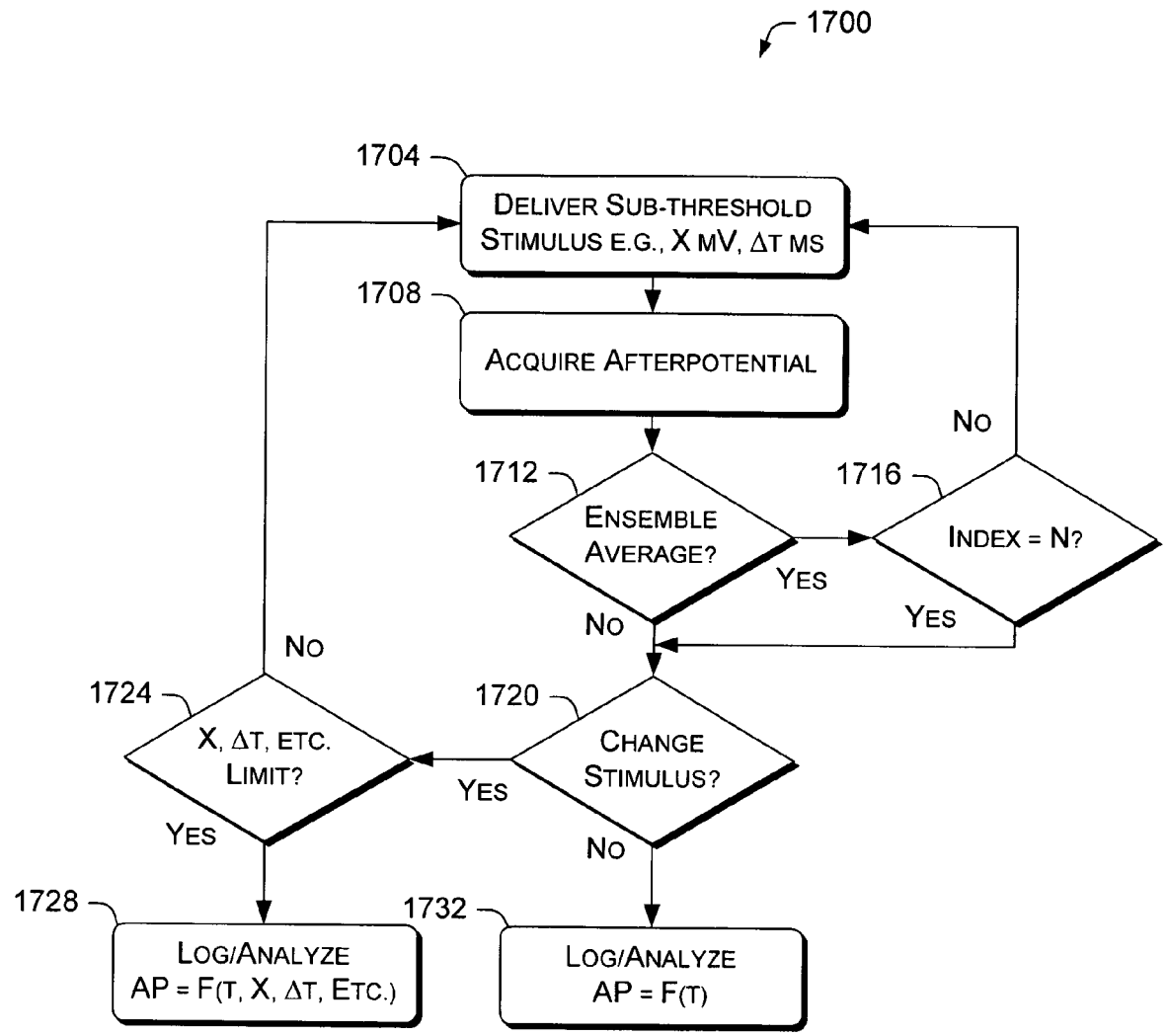
FIG. 17 is a block diagram of an exemplary method for analyzing afterpotential information.

Referring to FIG. 17, an exemplary method 1700 for acquiring afterpotential information is shown. In a delivery block 1704, an implantable pacing device delivers a sub-threshold stimulus (or alternatively a stimulus during a refractory period). Next, in an acquisition block 1708, which optionally follows a blanking period, the device acquires an afterpotential associated with the stimulus. The exemplary method 1700 then encounters a decision block 1712 to determine whether to ensemble average the acquired afterpotentials. If the decision block 1712 determines to ensemble average then yet another decision block 1716 determines whether N acquisitions have occurred. If N acquisitions have not occurred, then the method 1700 continues at the delivery block 1704; otherwise, another decision block 1720 follows. The method 1700 also continues to this decision block 1720 if ensemble averaging is not desired or operable. The decision block 1720 determines whether to change stimulus parameters such as, but not limited to, power. If the decision block 1720 determines not to change stimulus parameters, then the method 1700 ends in a log and/or analysis block 1732 wherein the device logs (e.g., stores) and/or otherwise analyzes the afterpotential with respect to time.

If the decision block 1720 decides to change stimulus parameters, then yet another decision block 1724 follows that determines whether some parameter limit has been reached and/or exceeded. If no limit has been reached, then the method 1700 changes the stimulus parameter and continues at the delivery block 1704. In the case that a limit is reached and/or exceeded per the decision block 1724, then the method 1700 ends in a log and/or analysis block 1728 wherein the device logs (e.g., stores) and/or otherwise analyzes the afterpotential with respect to time and/or stimulus parameters.

Figure 18:
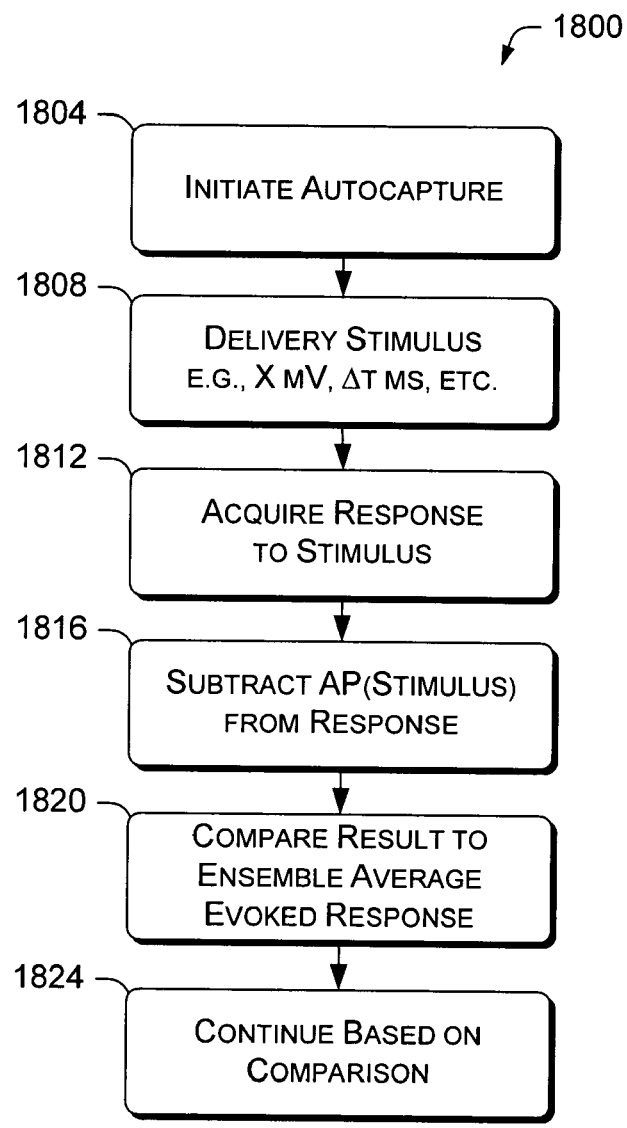
FIG. 18 is a block diagram of an exemplary method for using ensemble averaging and/or an ensemble average in an autocapture routine.

Referring to FIG. 18, an exemplary method 1800 for using ensemble averaging in an autocapture routine is shown. According to the exemplary method 1800, autocapture is initiated in an initiation block 1804. Next, a delivery block 1808 delivers a stimulus. Following stimulus delivery, an acquisition block 1812 acquires a response to the stimulus. A subtraction block 1816 follows wherein a known afterpotential corresponding, for example, to the stimulus of the delivery block 1808, is subtracted from the acquired response of the acquisition block 1812. After the subtraction block 1816, a comparison block 1820 compares the subtraction result to a known ensemble average evoked response that does not, for example, have any significant afterpotential artifact. The comparison may determine that, for example, capture, noncapture, fusion, pseudofusion, native activity, etc. occurred. The exemplary method 1800 continues, in a continuation block 1824, for example, on the basis of the comparison.

Figure 19:
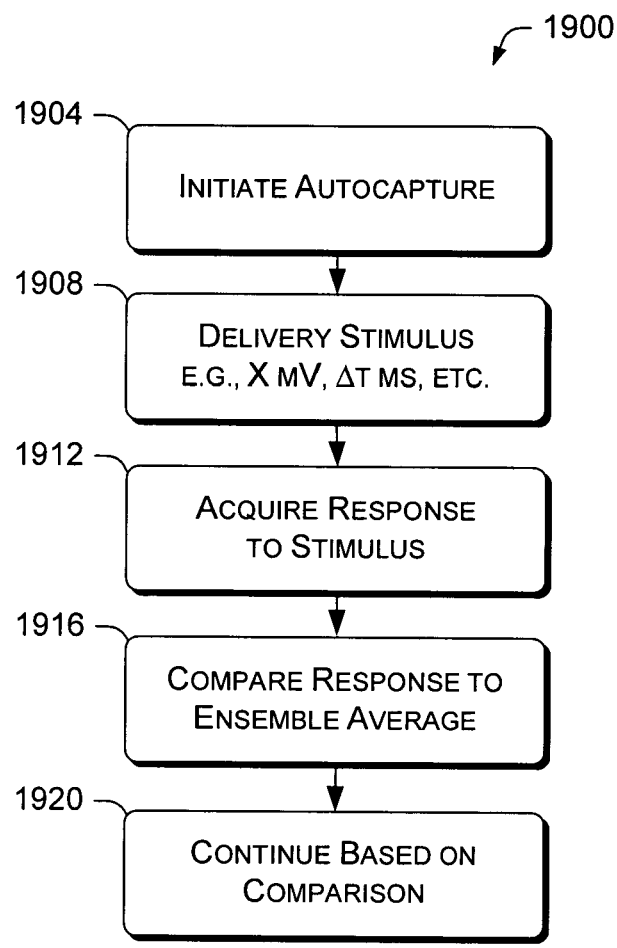
FIG. 19 is a block diagram of an exemplary method for using ensemble averaging and/or an ensemble average in an autocapture routine.
Figure 20:
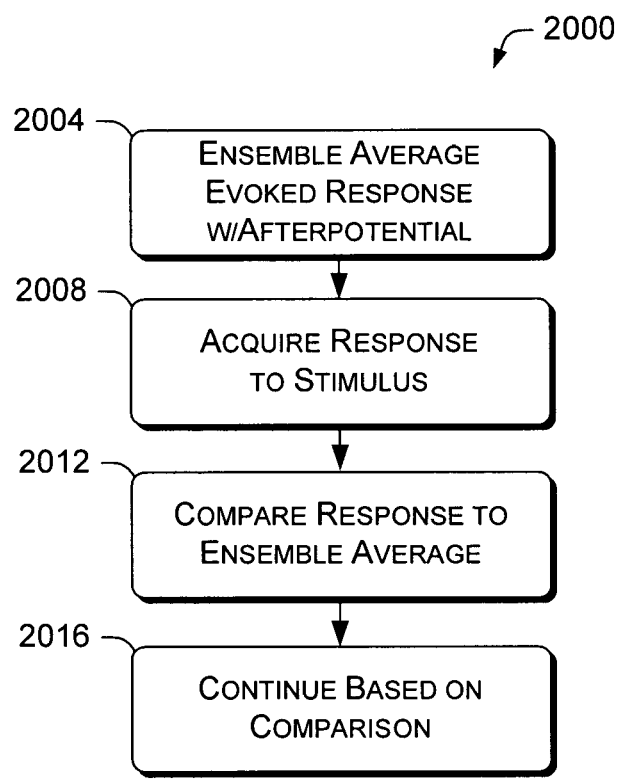
FIG. 20 is a block diagram of an exemplary method for using ensemble averaging and/or an ensemble average.

Referring to FIG. 19, another exemplary method 1900 for using ensemble averaging and/or an ensemble average in an autocapture routine is shown. In an initiation block 1904, an implantable pacing device initiates an autocapture routine. Next, in a delivery block 1908, the method 1900 delivers a stimulus. An acquisition block 1912 follows wherein the method 1900 acquires a response to the stimulus (e.g., IEGM). Next, in a comparison block 1916, the method 1900 compares the acquired response to a known ensemble average. The comparison may determine that, for example, capture, noncapture, fusion, pseudofusion, native activity, etc. occurred. The exemplary method 1900 continues, in a continuation block 1920, for example, on the basis of the comparison.

Various exemplary methods and/or devices are optionally used in conjunction with algorithms for determining capture thresholds and/or electrical stimulation levels. For example, such an algorithm may periodically perform an atrial or ventricular capture verification test and/or pacing threshold assessment test.

Various exemplary methods and/or devices may include an algorithm for determining a pacing energy stimulation threshold of a heart chamber. Such an algorithm may include a pulse generator that repeatedly applies pacing electrical pulse pairs to a particular chamber or chambers. In this example, each electrical pulse pair includes a first pulse and a second pulse, wherein the first pulse precedes the second pulse and is of lesser energy than the second pulse. Accordingly, the first and second pulses can evoke a first and a second response respectively. A subtractor can subtract the second response from the first response for each pulse pair to provide a series of capture values. A stimulation threshold may then be selected when the capture values change sign. When used with various exemplary methods and/or devices described herein, ensemble averages are optionally acquired in pairs, whether sequentially on a pulse-by-pulse basis or on a first series followed by a second series basis. Of course, more than a first and second ensemble average may be acquired. Further, atrial and ventricular ensembles may be acquired over an appropriate time interval. For example, a patient having some degree of block may require biventricular pacing. In such instances, an exemplary device may acquire ensemble averages for atrial evoked responses and ventricular evoked responses over an appropriate time interval wherein an atrial IEGM is acquired and then a ventricular IEGM is acquired. Whether acquired over the same time interval or not, a comparison may be made between single IEGMs and/or ensemble averaged IEGMs for atrial and/or ventricular activity.

CONCLUSION

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

What is claimed is:

1. A method comprising:
    delivering a first stimulus to a heart chamber and acquiring an intracardiac electrocardiogram that includes an evoked response;
    delivering a second stimulus to the heart that does not capture the heart, and acquiring an intracardiac electrocardiogram that includes an afterpotential;
    repeating the delivering of a first stimulus and the acquiring of an intracardiac electrocardiogram that includes an evoked response one or more times; and
    generating an ensemble average based on the intracardiac electrocardiograms that include evoked responses and that include an afterpotential.

2. The method of claim 1 wherein the delivering delivers an atrial stimulus and the acquiring acquires an atrial intracardiac electrocardiogram that includes an atrial evoked response.

3. The method of claim 1 wherein the delivering delivers a ventricular stimulus and the acquiring acquires a ventricular intracardiac electrocardiogram that includes a ventricular evoked response.

4. The method of claim 1, wherein the generating comprises subtracting the intracardiac electrocardiogram that includes an afterpotential and no evoked response from one or more of the intracardiac electrocardiogram that include an evoked response.

5. A method comprising:
    delivering a stimulus to a heart that does not result in capture;
    acquiring an intracardiac electrocardiogram responsive to the stimulus that includes an afterpotential;
    repeating the delivering and the acquiring one or more times; and
    performing an ensemble average of the intracardiac electrocardiograms.

6. The method of claim 5 wherein the delivering delivers an atrial stimulus and the acquiring acquires an atrial intracardiac electrocardiogram.

7. The method of claim 5 wherein the repeating repeats less than approximately 10 times.

8. The method of claim 5 wherein the acquiring follows a blanking period.

9. The method of claim 5 wherein the acquiring occurs within a time window.

10. The method of claim 5 further comprising excluding one or more of the intracardiac electrocardiograms from the performing on the basis of a criterion or criteria.

11. The method of claim 5 further comprising fitting the ensemble average to a model.

12. The method of claim 11 wherein the model includes an exponential.

13. The method of claim 5 further comprising changing power of the intracardiac stimulus.

14. The method of claim 13 wherein the changing follows the performing and further comprises repeating the delivering, the acquiring, the repeating and the performing.

15. The method of claim 13 further comprising analyzing one or more ensemble averages with respect to power of the intracardiac stimulus.

16. A method comprising:
    delivering a first stimulus to a heart chamber that results in capture of the heart tissue, and acquiring an intracardiac electrocardiogram that includes an evoked response;
    delivering a subthreshold stimulus to the heart, and acquiring an intracardiac electrocardiogram that includes an afterpotential;
    repeating the delivering of a first stimulus and the acquiring an intracardiac electrocardiogram that includes an evoked response one or more times; and
    generating an ensemble average based on the intracardiac electrocardiograms that include evoked responses and that include an afterpotential.

17. A device comprising:
    a lead adapted to contact heart tissue;
    a pulse generator adapted to deliver electrical stimulus to the lead; and
    a processor programmed to:
        control the pulse generator to deliver a plurality of first stimuli through the lead sufficient to capture the heart and at least one second stimulus through the lead insufficient to capture the heart;
        acquire a plurality of intracardiac electrocardiograms that include an evoked response;

acquire an intracardiac electrocardiogram that includes an afterpotential; and generate an ensemble average based on the intracardiac electrocardiograms.

18. A device comprising:

a lead adapted to contact heart tissue;

a pulse generator adapted to deliver electrical stimulus to the lead; and a processor programmed to:

control the pulse generator to deliver a plurality of stimuli through the lead insufficient to capture the heart;

acquire a plurality of intracardiac electrocardiograms that include an afterpotential; and ensemble average the intracardiac electrocardiograms.

* * * * *